US006797289B2

(12) United States Patent
Henderson et al.

(10) Patent No.: US 6,797,289 B2
(45) Date of Patent: Sep. 28, 2004

(54) USE OF ANABOLIC AGENTS, ANTI-CATABOLIC AGENTS, ANTIOXIDANT AGENTS, AND ANALGESICS FOR PROTECTION, TREATMENT AND REPAIR OF CONNECTIVE TISSUES IN HUMANS AND ANIMALS

(75) Inventors: Todd R. Henderson, Jarrettsville, MD (US); Tarek Hammad, Baltimore, MD (US); Medhat Soliman, Minya (EG); Barbara Corson, Fawn Grove, PA (US); Robert Henderson, Baldwin, MD (US)

(73) Assignee: Nutramax Laboratories, Inc., Edgewood, MD (US)

( * ) Notice: Subject to any disclaimer, the term of this patent is extended or adjusted under 35 U.S.C. 154(b) by 48 days.

(21) Appl. No.: 10/192,318

(22) Filed: Jul. 11, 2002

(65) Prior Publication Data

US 2003/0129261 A1 Jul. 10, 2003

Related U.S. Application Data (63) Continuation of application No. 09/274,881, filed on Mar. 23, 1999, and a continuation-in-part of application No. 09/249,335, filed on Feb. 12, 1999, now Pat. No. 6,451,771.
(60) Provisional application No. 60/088,205, filed on Jun. 5, 1998, and provisional application No. 60/074,594, filed on Feb. 13, 1998.

(51) Int. Cl.$^7$ .......................... A61K 35/78; A61K 31/70
(52) U.S. Cl. .......................... 424/757; 514/62; 514/23; 514/42
(58) Field of Search ............................ 514/62, 23, 42; 424/757

(56) References Cited

U.S. PATENT DOCUMENTS

| 2,881,173 A | 4/1959 | Wenner ................... 260/294.7 |
| 3,624,114 A | 11/1971 | Morelle ................... 260/402.5 |
| 3,882,228 A | 5/1975 | Boncey et al. ................. 424/35 |

(List continued on next page.)

FOREIGN PATENT DOCUMENTS

| EP | 0 609 001 A2 | 3/1994 | .......... A61K/31/23 |
| GB | 2 223 943 A | 4/1990 | .......... A61K/31/20 |

(List continued on next page.)

OTHER PUBLICATIONS

Piperno M., Reboul P., Helio Le Graverand M. P., et al; Glucosamine sulfate modulates dysregulated activities of human osteoarthritic chondrocytes in vitro; Osteoarthritis and Cartilage Journal of the OsteoArthritis Research Society International; (2000) 8, 207–212.

(List continued on next page.)

*Primary Examiner*—Shengjun Wang
(74) *Attorney, Agent, or Firm*—Covington & Burling (57) ABSTRACT

The present invention relates to compositions for the protection, treatment and repair of connective tissues in humans and animals comprising any or all of anabolic, anti-catabolic, anti-oxidant and analgesic agents, including aminosugars, S-adenosylmethionine, arachadonic acid, GAGs, including pentosan, collagen type II, tetracyclines or tetracycline-like compounds, diacerin, super oxide dismutase, L-ergothionine, one or more avocado/soybean unsaponifiables, and an analgesic, e.g., acetaminophen, and to methods of treating humans and animals by administration of these novel compositions to humans and animals in need thereof.

4 Claims, 5 Drawing Sheets

THE SYNTHESIS OF GLYCOSAMINOGLYCANS FROM GLUCOSAMINE

U.S. PATENT DOCUMENTS

| | | |
|---|---|---|
| 3,887,700 A | 6/1975 | Boncey et al. ................. 424/44 |
| 3,993,775 A | 11/1976 | Williams ..................... 424/312 |
| 4,100,160 A | 7/1978 | Walser ........................ 424/274 |
| 4,296,127 A | 10/1981 | Walser ........................ 424/317 |
| 4,309,415 A | 1/1982 | Horrobin ..................... 424/85 |
| 4,314,989 A | 2/1982 | Rosen .......................... 424/10 |
| 4,333,484 A | 6/1982 | Keritsis ....................... 131/359 |
| 4,386,072 A | 5/1983 | Horrobin et al. ........... 424/127 |
| 4,624,919 A | 11/1986 | Kokusho et al. .............. 435/74 |
| 4,683,298 A | 7/1987 | Yalpani ........................ 536/45 |
| 4,699,900 A | 10/1987 | Bayol et al. .................. 514/54 |
| 4,713,373 A | 12/1987 | Bayol et al. .................. 514/54 |
| 4,855,136 A | 8/1989 | Horrobin et al. ........... 424/602 |
| 4,900,724 A | 2/1990 | Kato et al. ..................... 514/62 |
| 4,925,833 A | 5/1990 | McNamara et al. ........ 514/152 |
| 4,994,457 A | 2/1991 | Crawford et al. .......... 514/22.6 |
| 5,084,482 A | 1/1992 | Hirsch et al. ................ 514/562 |
| 5,137,712 A | 8/1992 | Kask et al. ................... 424/10 |
| 5,145,841 A | 9/1992 | Cullis-Hill et al. ........... 514/54 |
| 5,215,759 A | 6/1993 | Mausner ..................... 424/489 |
| 5,225,192 A | 7/1993 | Lovrecich ................ 424/78.02 |
| 5,258,371 A | 11/1993 | Golub et al. ................ 514/152 |
| 5,262,163 A | 11/1993 | Rancurel |
| 5,288,503 A | 2/1994 | Wood et al. ................. 424/497 |
| 5,354,560 A | 10/1994 | Lovrecich ................... 424/489 |
| 5,354,853 A | 10/1994 | Staveski et al. ........... 536/17.1 |
| 5,364,845 A | 11/1994 | Henderson ................... 514/54 |
| 5,411,988 A | 5/1995 | Bockow et al. ............. 514/560 |
| 5,422,111 A | 6/1995 | Huc et al. ................... 424/401 |
| 5,449,521 A | 9/1995 | Lovrecich ................... 424/489 |
| 5,474,757 A | 12/1995 | Yang ........................... 514/562 |
| 5,480,873 A | 1/1996 | Brunavs et al. ............... 514/33 |
| 5,498,411 A | 3/1996 | Rancurel |
| 5,569,469 A | 10/1996 | Lovrecich ................... 424/501 |
| 5,587,363 A | 12/1996 | Henderson ................... 514/54 |
| 5,589,577 A | 12/1996 | Peltonen et al. ............ 536/221 |
| 5,658,767 A | 8/1997 | Kyle ........................... 435/434 |
| 5,668,172 A | 9/1997 | Gallagher et al. .......... 514/557 |
| 5,670,695 A | 9/1997 | Di Napoli ..................... 560/76 |
| 5,770,209 A | 6/1998 | Grotendorst et al. ..... 424/198.1 |
| 5,843,919 A | 12/1998 | Burger ......................... 514/62 |
| 5,891,465 A * | 4/1999 | Keller et al. ................. 424/450 |

FOREIGN PATENT DOCUMENTS

| | | | |
|---|---|---|---|
| WO | WO 88/07060 | 9/1988 | ........... C08B/37/02 |

OTHER PUBLICATIONS

Villani P., Bouvenot G.; Assessment of the Placebo Effect of symptomatic Slow–Acting Anti–Arthritics; Med. Presse Feb. 7, 1998; published on PubMed Central–indexed for MEDLINE.

Kirkpatrick, C.J. "Effects of Prostanoid Precursors and Indomethacin on Chick Embryonic Cartilage Growth in Organ Culture," Exp. Cell Biol., 51:1922–200 (1993).

Kent, L. et al., "Differential Response of Articular Chondrocyte Populations to Thromboxane B2 and Analogs of Prostaglandin Cyclic Endoperoxidases," Prostaglandins, 19:391–406 (1980).

Kirkpatrick C. J. and Gardner, D.L., "Influence of PGA1 on Cartilage Growth," Experientia, 33 (4): 504 (1976).

Pipitone, V.R. "Chondroprotection With Chondrotin Sulfate", Drugs under Research, Druges Exptl. Clin Res XVII(1) 3–7, 1991.

Champe, P. Biochemistry, 2nd Edition, J.B. Lippincott Co., Philadelphia, 1994, pp. 248, 250, 265.

Nakamura, M., "Archindonic Acid Stimulates Corneal Epithelial Migration" J. Ocul. Pharmacol., summer: 10(2): 453–9 abstract.

Bartolucci, C., "Chondroprotective action of chondroitin sulfate," Int. J. Tiss. Reac., XIII (6) 311–317 (1991).

Kilgore, K., "The Semisynthetic Polysaccharide Pentosan Polysulfate Prevents Complement–Mediated Myocardial Injury in the Rabbit Perfused Heart" J. Pharmocol, Exp. Ther., 285 (3): 987–94 (1998) abstract.

Ryan, M., "Potential of Tetracyclines to Modify Cartilage Breakdown in Osteoarthritis," Curr. Opin. Rheumatol., 8 (3): 238–47 (1996) abstract.

Beccerica, E., "Diacetylrhein and rhein: in vivo and in vitro effect on lymphocyte membrane fluidity," Pharmocol. Res., 22(3): 277–85 (1990) abstract.

Mian, M., "Experimental Studies on Diacerhein: Effects on the Phagocytosis of Neutrophil Cells from Subcutaneous Carregeenan–Induced Exudate," Drugs Exp. clin. Res., 13(11): 695–8 (1987) abstract.

Spencer, C., "Diacerein", Drugs, 53(1): 98–106 (1997).

Han JS, "Effects of Various Chemical Compunds on Spontaneous and Hydrogen Peroxide Induced Reversion in Strain TA104 of *Salmonella typhimuriu*", Mutant Res., 266(2): 77–84 (1992) abstract.

Mathews C., *Biochemistry* 2nd ed., Benjamin/Cummings pub. co., Menlo Park CA, p551 (1996).

Arduini, A. "Possible Mechanism of Inhibition of Nitrite–Induced Oxidation of Oxyhemoglobin by Ergothioneine and Uric Acid," Arch. Biochem. Biophys., 294(2): 398–402 (May 1992). abstract.

Baldessarini, F., "Neuropharmacology of S–Adenosyl Methionine," American J. Med., 83(5A): 95–103 (1987).

Brummel, M.C., "In Search of a Physiological Function for L–ergothioneine," Med. Hypotheses, 18(4): 351–70 (Dec. 1985). abstract.

Brummel, M.C., "In Search of a Physiological Function for L–ergothioneine,—II," Med. Hypotheses, 30(1): 39–48 (Sep. 1989).

Carney, M., "Neuropharmacology of S–Adenosyl Methionine," Clin. Neuropharmacol., 9(3): 235–243 (1986).

Hardingham, T.E., et al., "Proteoglycans: Many Forms and Many Functions," FASEB J., 6:861–862 (1992). abstract.

Janicak, P., "S–Adenosylmethionine in Depression," Alabama J. Med. Sci. 25(3): 306–313. (1988).

Morrison, L.M., MD, et al., Coronary Heart Disease and the Mucopolysaccharides (Glycosaminoglycans) (1974).

Phan, S,H., et al., Regulation of MO–derived FGF Release by Arachadonate Metabolites, J. Leukoc Biol. 42(2): 106–13 (Aug. 1987). abstract.

Stramentinoli, G., "Pharmacologic Aspects of S–Adenosyl-methionine," American J. Med., 83(5A): 35–42. (1987).

Yu, LP Jr., et al., "Effects of oral doxycycline administration on histomorphometry and dynamics of subchondral bone in a cannie model of osteoarthritis," J Rheumatol Jan. 1996; 23(1):137–42. abstract.

Amin, AR et al., "A novel mechanism of action of tetracyclines: effects on nitric oxide synthases," Proc Natl Acad Sci USA Nov. 26, 1996; 93(24):14014–9. abstract.

Beekman B. et al., "Doxycycline inhibits collagen synthesis by bovine chondrocytes cultured in alginate," Biochem Biophys Res Commun Aug. 8, 1997; 237(1):107–10. abstract.

Smith GN Jr et al., "Oral administration of doxycycline reduces collagenase and gelatinase activities in extracts of human osteoarthritic cartilage," J Rheumatol Mar. 1998;25(3):532–5. abstract.

Brandt KD, "Compensation and decompensation of articular cartilage in osteoarthritis," Agents Actions Nov. 1993; 40(3–4):232–4. abstract.

Pomarelli P. et al., "A non steroidal anti–inflammatory drug that stimulates prostaglandin release," Farmaco [Sci] Oct. 1980; 35(10):836–42. abstract.

La Villa G. et al., "Effects of rhein on renal arachidonic acid metabolism and renal function in patients with congestive heart failure," Eur J Clin Pharmacol 1989; 37(1):1–5 . abstract.

Debord P et al., "Influence of renal function on the pharmacokinetics of diacerein after a single oral dose," Eur J Drug Metab Pharmacokinet Jan.–Mar. 1994; 19(1):13–9. abstract.

Nguyen M et al., "Diacerhein in the treatment of osteoarthritis of the hip," Arthritis Rheum Apr. 1994; 37(4):529–36 abstract.

Brandt KD et al., "Effects of diacerhein in an accelerated canine model of osteoarthritis," Osteoarthritis Cartilage Nov. 1997; 5(6):438–49. abstract.

Martel–Pelletier J et al., "In vitro effects of diacerhein and rhein on interleukin 1 and tumor necrosis factor–alpha systems in human osteoarthritic synovium and chondrocytes," J Rheumatol Apr. 1998;25(4):753–62. abstract.

Moore AR et al., "Effects of diacerhein on granuloma induced cartilage breakdown in the mouse," Osteoarthritis Cartilage Jan. 1998; 6(1):19–23. abstract.

Pietrangelo A et al., "Diacerhein blocks iron regulatory protein activation in inflamed human monocytes," Life Sci 1998;63(14):PL213–9. abstract.

Nicolas P et al., "Clinical pharmacokinetics of diacerein." Clin Pharmacokinet Nov. 1998;35(5):347–59 abstract.

Jepsen JV et al., "Long–term experience with pentosanpolysulfate in interstitial cystitis," Urology Mar. 1998; 51(3):381–7 abstract.

Degenhardt M et al., "Quality control of pentosane polysulfate by capillary zone electrophoresis using indirect detection," J Chromatogr A Aug. 21, 1998; 817(1–2):297–306. abstract.

Yunmbam MK, "Inhibition of breast cancer in nude mouse model by anti–angiogenesis," Oncol Rep Nov.–Dec. 1998;5(6):1431–7. abstract.

Marshall JL et al., "Phase I Trial of Orally Administered Pentosan Polysulfate in Patients with Advanced Cancer," Clin Cancer Res Dec. 1997; 3(12):2347–2354. abstract.

Khaled Z et al., "Effects of Suramin–related and Other Clinically Therapeutic Polyanions on Protein Kinase C Activity," Clin Cancer Res Jan. 1995; (1): 113–122. abstract.

Retzinger GS et al., "Adsorption of fibrinogen to droplets of liquid hydrophobic phases : functionality of the bound protein and biological implications," Arterioscler Thromb Vasc Biol Dec. 1998;18(12):1948–57. abstract.

Paulikova H et al., "The effect of heparin and pentosan polysulfate on the thermal stability of yeast alcohol dehydrogenase," Biochem Mol Biol Int Dec. 1998;46(5):887–94. abstract.

Wallace JL et al., "Comparison of the damage–promoting effects of leukotrienes derived from eicosapentaenoic acid and arachidonic acid on the rat stomach," J Exp Med May 1, 1990:171(5):1827–32. abstract.

Hebborn P et al., "Action of topically applied arachidonic acid on the skin of patients with psoriasis," Arch Dermatol Mar. 1988; 124(3):387–91. abstract.

Smith, R.C. et al, "Inhibition by thiols of copper(II)–induced oxidation of oxyhemoglobin", Chem Biol Interact Apr. 15, 1992; 82(2); 209–17 (abstract).

Srinivasan BD, "Corneal reepithelialization and anti–inflammatory agents," Trans AM Ophthalmol Soc 1982; 80:758–822. abstract.

Robertson JT, "Prostaglandin production after experimental discectomy," Spine Aug. 1, 1996;21(15):1731–6. abstract.

Katori M, Majima M , "[Multiple roles of inducible cyclooxygenase–2 and its selective inhibitors]," Nippon Yakurigaku Zasshi Jun. 1997;109(6):247–58. abstract.

Mooney MA et al., "Evaluation of the effects of omega–3 fatty acid–containing diets on the inflammatory stage of wound healing in dogs," AM J Vet Res Jul. 1998;59(7):859–63. abstract.

Morykwas MJ et al., "Arachidonic acid metabolites: effects on inflammation of fetal rabbit excisional wounds," Inflammation Jun. 1992;16(3):251–8. abstract.

Rovati, LC, "The Practical Clinical Development of a Selective Drug for Osteoarthritis: Glucosamine Sulfate," Eular '96 IX Symposium, Madrid, Oct. 7–10, 1996.

Jimenez SA, Dodge GR,"The Effects of Glucosamine Sulfate on Chondrocyte Gene Expression," Eular '96 IX Symposium, Madrid, Oct. 7–10, 1996.

Hellio MP et al., "The Effects of Glucosamine Sulfate on Human Osteoarthritic Chondrocytes in Vitro Investigations," Eular '96 IX Symposium Madrid, Oct. 7–10, 1996.

Dougados Maxime, "The current Classification of Drugs in Osteoarthritis and the Recommendations for their Development," Eular '96 IX Symposium Madrid, Oct. 7–10, 1996.

Artrodar Diacerein.

"Fatty Acids in Foods and Their Health Implications.".

Galli, C, Dietary Omega 3 and Omega 6 Fatty Acids, Biological Effects and Nutritional Essentialiaty, 297–307, Plenum Press.

Matthews, C.K. & van Holde, K.E. *Biochemistry* 2nd ed., The Benjamin/cummings Pub. Co., 1996, p. 691.

Thiers, M. H. "Unsaponifiable constituents of avocado and soya oils. Treatment of certain forms of arthralgia," J. Med. Lyon 53 (222): 195–8 (Feb. 1972) (English summary, p. 198.).

Trevoux, R., "Unsaponifiable fractions of the avocado and soybean in gynecology," *J. Bynecol. Obstet. Biol. Reprod.* 6(1): 99–105 (Jan. 1977) (article in French) (English abstract).

Lamaud, M.E., et al., "Biochemical modifications of connective tissue induced by the non–saponifiables of avocado and soy–bean oils administered percutaneously in the 'hairless' rat," *Pathol. Biol.* 26 (5):269–74. abstract.

Boumediene K., et al., "Avocado/soya unsaponifiables enhance the expression of transforming growth factor beta 1 and beta 2 in cultured articular chondrocytes," *Arthritis Rheum.* 42 (1): 148–56 (Jan. 1999) abstract.

Henrotin, Y.E., et al., "Effects of three avocado/soybean unsaponifiabl e mixtures on metalloproteinases, cytokines and prostaglandin E2 production by human articular chondrocytes," Clin. Rheumatol. 17(1): 31–9 (1998). abstract.

Cotran R., et al., *Pathologic Basis of Disease*, 5th ed., Saunders, 1994, pp 40–41.

Maheu, E., et al., "Symptomatic efficacy of avocado./soybean unsaponifiables in the treatment of osteoarthritis." Arthritis Rheum. 41 (1): 81–91 (Jan. 1998).

Blotman, F., et al.., "Efficacy and safety of avocado/soybean unsaponifiables in the treatment of symptomatic osteoarthritis," Rev. Rheum. Engl. Ed. 64(12): 825–34.

Goodman, A., and Gillman, L., The Pharmacological Basis of Therapeutics, 7th ed., MacMillan Publishing co., 1985, pp 692–95.

Ahrens, F., Pharmacology, Williams & Wilkins, 1996, pp 174–75.

Champe, P., and Harvey, R.A., Glycosaminoglycans Lippincott's Illustrated Reviews: Biochemistry, p148–151 (2nd ed. 1994).

Lieber, C.s., "Biochemical Factors in Alcoholic Liver Disease," Seminars in Liver Disease, 13:2, 1993, Theime Medical Publishers, Inc., New York, NY. abstract.

Cotran et al., Pathologic Basis of Disease, 1994, p 423.

Girre, C., et al., "Increased Metabolism of Acetaminophen in Chronically Alcoholic patients," Alcohol Clin. Exp. Res. (Feb. 1993) 17(1): p170–3. abstract.

Rose, S.R., "Subtleties of Managing Acetaminophen Poisoning," Am. J. Hosp. Pharm. (Dec. 15, 1994) 51(24): p3065–8.

Barker, J.D., et al., "Chronic Excessive Acetaminophen Use and Liver Damage," Ann. Inern. Med. (Sep. 1977) 87(3): p299–301. abstract.

Fry, S.W., and Seef, L.B., "Hepatotoxicity of Anagesics and Anti–Inflammatory Agents" Gastroenterol. Clin. North Am. (Dec 1995) 24(4): p 875–905. abstract.

Lindgren, A. et al., "Paracetamol–inducted Cholestatic and Granulomatous Liver Injuries," J. Intern. Med. (May 1997) 241(5): p435–9. abstract.

Van der Kraan, P.M. et al., "The Effect of Chronic Paracetamol Administration to Rats on the Glycosaminoglycan Content of Patellar Cartilage," Agent Actions (Mar. 1990); 29 (3–4): p 218–223. abstract.

Beren, J., et al., Therapeutic Effect of Cosamin on Autoimmune Type II Collagen Induced Arthtritis in Rats. Proceedings of the north American Veterinary conference (Innovations and New Product Applications in Veterinary Practice) Jan. 1997, p 35. abstract.

Hulse, D., "Treatment Methods for Pain in the Osteoarthritic Patients." In the veterinary clinics of N. America, small animal practice clinical pharmacology and therapeutics. vol. 28 (2) p 373.

Bucci, L. "Chondroprotective agents: Glucosamine Salts and Chondroitin Sulfates," Townsend Letter for Doctors, Jan. 1994, pp. 52–54.

Ettinger, WH. et al., Physical Disability from Knee Osteoarthritis: The Role of Excerciese as an Intervention. Medical Science Sports Exercise Dec ; (1994) 26 (12): p 1435–1440. abstract.

Fransen M., et al., "A Revised Group Exercise Program for Osteoarthritis of the Knee" Physiother Res Int 2 (1): p 30–41. abstract.

Hanson RR et al., "Oral Treatment With a Glucosamine–chondroitin sulfate compound for DJD in Horses: 25 cases" Equine Practice, 1997; p 16–22.

Hanson RR et al., "Oral Glycosaminoglycans in Treatment of Degenerative Joint Disease in Horses", Equine Practice, vol 18, No. 10 Nov./Dec./1996. pp 18–22.

Hartman, PE et al., "Direct interception of mutagens and carcinogens by biomolecules", Basic Life Sci 1993:61:35—66, abstract.

Todhunter RJ et al., "Effects of Exercise and Polysulfated Glycosaminoglycan on the Development of Osteoarthritis in Equine Carpal Joints With Osteochondral Defects." Vet Surgery; 22 (5); p 330–342. abstract.

Vam Der Kraan, PM, et al., "Inhibition of Glycosaminoglycan Synthesis in Anatomically Intact Rat Patellar Cartilage by Paracetamol–induced Serum Sulfate Depletion." Biochem Pharmacol; 37 (19): p 3683–3690. abstract.

Van der Kraan, PM et al., "The Effect of chronic Paracetamol Administration to Rats on the Glycosaminoglycan Content of Patellar Cartilage," Agents Actions, Mar. 1990; 29(3–4): p 218–223. abstract.

Miller et al., Treatment of Dogs With Hip Arthritis With a Fatty Acid Supplement, Canine Practice, vol 17. No. 6, Nov./Dec. 1992, pp 6–8.

Barcelo et al., "Effect of S–Adenosylmethionine on Experimental Osteoarthritis in Rabbits," The American Jounrnal of Medicine, Nov. 20, 1987, vol. 83 (suppl 5A) pp 55–59.

Di Padova, C., "S–Adenosylmethionine in the Treatment of Osteoarthritis," The American Journal of Medicine, Nov. 20, 1987 vol. 83 (suppl 5A), 60–65.

Berger et al., "A New Medical Approach to the Treatment of Osteoarthritis," The American Jouurnal of Medicine, Nov. 20, 1987, (suppl 5A), 84–88.

Oyanagui, Y., "Inflammation and Superoxide Production by Macrophages", Trends in Inflammation Research 1, Agents Acions Suppl 1980;7:174–179.

Borrelli F. et al., "Additional Pharmacological Aspects of Orgotein, A Metalloprotein with Superoxide–Dismutase Activity," Arzneimittelforschung, 1979, 29/I. 781–785.

McCord, J.M., "Phagocyte–produced Free Radicals: Roles in Cytotoxicity and Inflammation," Ciba Foundation Symposium 65. Excerpts Medica, Amsterdam–Oxford–New York, 1979, 343–360.

Paroli, E., et al. "A Pharmacological Approach to Glycosaminoglycans," Drugs Under Experimental and Clinical Research, 1991; 17 (1), 9–19.

Boothe, D. et al., "Round Table Discussion of Degenerative Joint Disease in Dogs," Canine Practice. 21(1–4) 1–16, Jan./Feb.–Jun./Jul., 1996.

Anderson, M.A. et al., "Results of a Survey of Small–Animal Practitioners on the Percieved Clinical Efficacy and Safety of an Oral Nutraceutical." Proceedings of AcVS, Orlando, Oct. 1997 (in press), abstract.

McNamara, P. et al., "Hematologic, Hemostatic, and Biochemical Effects in Dogs Receiving an Oral Chondroprotective Agent for Thirty Days." Am. J. Vet. Res., 57(9): 1390–1394, 1996. abstract.

Roden, Lennart, "Effect of Hexosamines on the Synthesis of Chondroitin Sulphuric Acid in Vitro," Ark. Kemi., 10, 345–352, 1984. abstract.

Trentham, David E., "Evidence That Type II Collagen Feeding Can Induce a Durable Therapeutic Response in Some Patients With Rheumatoid Arthritis," Ann N.Y. of Academy Sciences, 778–306–14, 1996.

Hartman Philip E., "Ergothioneine as Antioxidant," Methods in Enzymology, vol. 186, 310–318, Academic Press, Inc. 1990.

Huber, W., "Orgotein–(bovine Cu–Zn superoxide dismutase), an anti–inflammatory protein drug; discovery toxicology and pharmacology," Eur. J. Rheumatol. Inflamm., 1981; 4(2): 173–82.

Lippiello L., "Lipid and cell metabolic changes associated with essential fatty acid enrichment of articular chondrocytes", In: Chondrocyte Response to Lipid Loading, Society for Experimental Biology and Medicine, Jun. 1990.

Koopman, W.J., Arthritis and Allied Conditions, ATextbook of Rheumatology, 13th ed., Vol. 2, 2020–2022.

Ghosh, P., Smith, M. and Wells, C. "Second–Line Agents in Osteoarthritis." In: Second–Line Agents in the Treatment of Rheumatic Diseases. Marcel–Dekker, Inc. New York, 353–427, 1992.

Brooks, P.M., "Clinical management of rheumatoid arthritis," The Lancet, vol. 341, 286–290.

Huber, W., et al., "Superoxide Dismutase Pharmacology and Orgotein Efficacy: New Perspectives," In: Biological and Clinical Aspects of Superoxide and Superoxide Dismutase. Developments in Biochemistry (Banniser, W.H., Bannister, J.V., eds., Elsevier, New York–Amsterdam–Oxford 1980 vol. II B, 395–407.

Lippiello, Louis, "Prostaglandins and articular cartilage metabolism: Does prostaglandin perturbation perpetuate cartilage destruction?," Osteoarthritis Symposium, University of Nebraska Medical Center, Omaha Nebraska, pp 87–88.

Clark, D.M. , DVM, "The Biochemistry of Degenerative Joint Disease and Its Treatment," Continuing Education Article #9, vol. 13, No. 2, Feb. 1991 pp. 275–281.

Katzung, MD, PhD., Bertram G., (1995) : Other Analgesics, Acetaminophen. In Basic and Clinical Pharmacology. Appleton and Lang. 551–2.

Hulse, DS, Hart D, SlatterM, Beale BS, "The Effect of Cranial Cruciate Deficient and Reconstructed Stifle Joints in Dogs," Proceedings of the veterinary Orthopedic Society, San Francisco, CA (1998 (in press).

Lindh C., Liu Z, Lyrenas S. Ordeberg G, Nyberg F. (1997) : "Elevated cerebrospinal fluid substance P–like immunoreactivity in patients with painful osteoarthritis, but not in patients with rhizopatic pain from a herniated lumbar disc," Scand J Rehumatol; 26(6): 468–72.

Ackerman, Lowell, "Reviewing the Biochemical Properties of Fatty Acids," Veterinary Medicine, Dec. 1995.

Ackerman, Lowell, "Detmatologic Uses of Fatty Acids in Dogs and Cats," Veterinary Medicine, Dec. 1995.

Trentham, D.E. et al., "Effects of Oral Administration of Type II Collagen on Rheumatoid Arthritis," Science. vol. 261, Sep. 24, 1993, p 1727–30.

Newton, G.L. et al., "Low–molecular–weight thiols in streptomycetes and their potential rule as antioxidants", J Bacteriol May 1993: 175(9):2734–42. abstract.

Mimata, H. et al., "Effects of thiols on prostaglandin synthesis in bovine bladder–epithelium", Urol Int 1993:50(3):129–32. abstract.

Aruoma, O I et al., Antioxidant action of ergothioneine: assessment of its ability to scavenge peroxynitrite, Biochem Biophys Res Commun Feb 13, 1997: 231(2) 389–91. abstract.

Asmus, K.D. et al., "One–electron oxidation of ergothioneine and analogues investigated by pulse radiolysis: redox reacton involving ergothioneine and vitamin C", Biochem J Apr. 15, 1996: 315 (Pt 2):625–9, abstract.

Egorov S Yu et al., "Quenching of singlet molecular oxygen by conrosine and related antioxidants. Monitoring 1270–nm phosphorescence in aqueous media", Biochem Mol Biol Int 1997 Ap441(4):687–94, abstract.

Shires T.K., et al., "Egothioneine distribution in bovine and procine ocular tissues", Comp Biochem Physiol C Pharmacol Toxicol Endocrinol May 1997 117(2): 117–20. abstract.

Scharrer E. et al., "Stimulation of mucosal uptake of selenium from selenite by some thiols at various sites of rat intestine", Biol Trace Elem Res Apr.–Jun. 1992:33: 109–20. abstract.

Cargoni A. et al., "In vitro administration of ergothioneine failed to protect isolated ischaemic and reperfused rabbit heart", Biochem Biophys Acta Apr. 24, 1995:1270(2–3): 173–8. abstract.

Hanson, R.R., et al., "The Clinical Profile of a Glucosamine–Chondroitin Sulfate Compound in a Double–Blinded, Placebo–Controlled, Randomized Trial as a Selective Symptom Modifying Nutraceutical for Navicular Syndrome: Current Data and Perspectives," Veterinary OrthopedicSociety, 25th Annual Conference, Snowmass, Colorado (Feb. 21–28, 1998).

Lance, R., Ph.D., et al., "Drug Information Handbook," Lexi–Comp. Inc., American Pharmaceutical Associate, 4; 1–3; 12–15 (1997–98).

Lippiello, L. et al., "Modification of Articular Cartilage Chondrocyte Metabolism by in Vitro Enrichment with Fatty Acids," Trans. Orthop. Res. Soc., 12: 162 (1998).

Lippiello, L. et al., "Cartilage Stimulatory and Antiproteolytic Activity is Present in Sera of Dogs Treated with a Chondroprotective Agent," Canine Practice, 24(1) (Jan./Feb. 1999).

Hanson, R.R. et al., "Evaluation of the Clinical Efficacy of a Nutraceutical in the Treatment of Navicular Syndrome: A Double–Blinded Placebo–Controlled Randomized Clinical Trial," ACVS Veterinary Symposium, ACVS Abstract No. 38, pp. 9–10 (Oct. 16–19, 1997).

McNamara, P.S. et al., "Effects of an Oral Chondroprotective Agent (Cosequin) on Cartilage Metabolism and Canine Serum," Veterinary Orthopedic Society, 24th Annual Conference, p. 35 ( Mar. 1–8, 1997).

McNamara, Paul S., DVM, et al., "Slow–Acting Disease–Modifying Osteoarthritis Agents," Veterinary Clinics of North America: Small Animal Practice, 27(4): 863–867 (Jul. 1997).

Hardie, Elizabeth M., DVM, "Slow–Acting Disease–Modifying Osteoarthritis Agents," Veterinary Clinics of North America: Small Animal Practice, 27(4): 950–952.

* cited by examiner

FIG. 1

THE SYNTHESIS OF GLYCOSAMINOGLYCANS FROM GLUCOSAMINE

FIG. 2

THE SYNTHESIS OF S-ADENOSYLMETHIONINE

FIG. 3

SIMPLIFIED DIAGRAM OF THE THREE-DIMENSIONAL STRUCTURE OF A SUBUNIT OF BOVINE SUPEROXIDE DISMUTASE

Lycopene

Gibberellic acid

Limonene

α-Tocopherol (vitamin E)

Phylloquinone

Examples of unsaponifiable lipids

USE OF ANABOLIC AGENTS, ANTI-CATABOLIC AGENTS, ANTIOXIDANT AGENTS, AND ANALGESICS FOR PROTECTION, TREATMENT AND REPAIR OF CONNECTIVE TISSUES IN HUMANS AND ANIMALS

CROSS-REFERENCE TO RELATED APPLICATIONS

This application is a continuation application of U.S. application Ser. No. 09/274,881, filed Mar. 23, 1999, which is a continuation-in-part of U.S. patent application Ser. No. 09/249,335 filed Feb. 12, 1999 now pat. No. 6,451,771 which claims benefit of U.S. patent No. 60/088,205 filed Jun. 5, 1998 and which claims benefit of U.S. patent No. 60/074,594 filed Feb. 13, 1998. which claims the priority to the following provisional application, A COMPOSITION OF ACETAMINOPHEN, AN AMINOSUGAR AND A GLYCOSAMINOGLYCAN, U.S. Ser. No. 60/088,205, filed Jun. 5, 1998. The present application is also a continuation-in-part application of U.S. patent application Ser. No. 09/249,335, filed Feb. 12, 1999, now U.S. Pat. No. 6,451,771, the disclosure of which is hereby incorporated by reference herein in its entirety. That application claimed priority to provisional application: THE USE OF ANABOLIC AGENTS, ANTI-CATABOLIC AGENTS, ANTIOXIDANT AGENTS, AND ANALGESICS FOR PROTECTION, TREATMENT AND REPAIR OF CONNECTIVE TISSUES IN HUMANS AND ANIMALS, U.S. Ser. No. 60/074,594, filed Feb. 13, 1998.

FIELD OF THE INVENTION

The present invention relates to compositions for the protection, treatment and repair of connective tissues in humans and other animals.

BACKGROUND OF THE INVENTION

The tissues of mammals, including humans, are in a constant state of flux between the anabolic processes that build up tissues, and the catabolic processes which degrade tissues. The state of health exists when there is a balance between these two processes, and derangements of the balance produce disease. This holds true for all tissues of the body. Connective tissues are of particular importance for several reasons. First, they support the "functional cells" of the body, i.e., epithelial, muscle and neural cells. Second, they play critical roles in intercellular communication, which is essential for multicellular life.

The inflammatory process occupies a key position in this balance. When injury to tissues occurs, inflammation initiates the biochemical processes that result in tissue repair. Because inflammation results in the symptoms of pain, inflammation, and swelling of the tissues involved, it is often regarded by both patients and physicians as an abnormal and undesirable state, which should be treated and relieved as soon and as completely as possible. As a result, pharmacies are full of "anti-inflammatory drugs" (such as corticosteroids and the non-steroidal anti-inflammatory drugs, such as aspirin). Under certain circumstances, inflammation can indeed be destructive; however, it is important to remember that inflammation is closely linked with tissue healing. Indeed, inflammation is not easily categorized as strictly anabolic or catabolic—it may have either effect. Its purpose in the body is to remove, dilute or wall-off the injurious agent(s). It also sets into motion the biochemical processes that repair and reconstruct the damaged tissue. Because it is essential to healing, and because it can also cause tissue destruction, inflammation and its mediators are important factors in the anabolic and catabolic balance.

One very important class of inflammatory mediators is the eicosanoid group. The eicosanoids are synthesized in the body from essential fatty acids ("FAs"). Through a series of biochemical reactions, the precursor fatty acids are modified to produce intermediate metabolites, arachadonic acid ("AA"), an omega-6 FA; and eicosapentanoic acid ("EPA"), an omega-3 FA. Eicosanoids produced from arachidonic acid include the 2-series of prostaglandins and the 4-series of leukotrienes, which are generally proinflammatory. The eicosanoids derived from EPA, such as the 3 series prostaglandins and hydroxyeicosapentaenoic acid ("HEPE"), are less inflammatory than those derived from AA. In addition, such eicosanoids may even have anti-inflammatory effects.

As a class, the eicosanoids are short-lived and locally active. They are responsible for the initial events of inflammation, including vasodilation, increased vascular permeability, and chemotaxis. Moreover, the eicosanoids are instrumental in the early steps of the healing process. For example, the eicosanoids trigger the release of cytokines such as TGF-B, which in turn stimulates the migration and proliferation of connective tissue cells, and the deposition of extracellular matrix. Specific constitutive eicosanoids also have protective effects in the gastrointestinal mucosa and kidney, because they maintain glycosaminoglycan synthesis and normal perfusion of these organs.

Because of anabolic processes such as these, and because of the influence of natural anti-catabolic and anti-oxidant agents in the body, the outcome of the majority of cases of inflammation is resolution of the injury and healing of the damaged tissues. Only in pathologic situations does inflammation itself become a contributor to disease.

Research on the therapeutic use of eicosanoid precursor FAs (including cis-linoleic and alpha-linolenic acids, the so-called omega-3 and omega-6 fatty acids) has been primarily directed towards their use as competitive inhibitors of the synthesis of eicosanoids, and therefore, their anti-inflammatory effects. Except in cases of severe or absolute dietary deficiency, little attention has been given to the beneficial, anabolic effects that the eicosanoids have in connective tissues. However, naturally occurring "subclinical" deficiencies of eicosanoids probably contribute significantly to disease, and are under diagnosed. For example, the enzyme delta-6-desaturase is responsible for the committed step in the synthesis of AA. Activity of this enzyme, (delta-6-desaturase) decreases with age. This is likely to prove a significant factor in the increased incidence of connective tissue dysfunction in older population segments since a deficiency of AA would decrease anabolic processes and allow catabolic events to dominate.

Given the importance of inflammation in the healing of tissues, and the protective role that some eicosanoids play, it is not surprising that pharmaceuticals that decrease inflammation by blocking eicosanoid production should also have negative effects on healing and anabolic processes. It has long been known that corticosteroid drugs, which are strongly anti-inflammatory, also delay healing and decrease the production of extracellular matrix components. This is because cortisol and related compounds stabilize cell membranes and therefore inhibit the release of phospholipase A2, the precursor of AA. Recently attention has turned to the non-steroidal anti-inflammatory drugs ("NSAIDs"). Numerous studies have shown that NSAIDs, like corticosteroids, can decrease the synthesis of matrix components by connective tissue cells, because they inhibit prostaglandin endoperoxide synthase, and thus block the cyclooxygenase pathway.

Since the inflammatory process is the sine qua non of tissue healing, and since the eicosanoids are the mediators of the inflammatory process, the use of AA (and other eicosanoid compounds) is a novel approach to therapy of injured tissues. Kirkpatrick et al. investigated the use of prostanoid precursors on chick embryonic cartilage in organ culture and found no significant effects. [Kirkpatrick, C. J., "Effects of Prostanoid Precursors and Indomethacin on Chick Embryonic Cartilage Growth in Organ Culture," *Expl. Cell Biol.* 51:192–200 (1993)]. The experimental model in this work may have contributed to the absence of significant effects, because avian cartilage and embryonic cartilage differ significantly from mammalian, postnatal cartilage. For example, embryonic cartilage of any species is hypermetabolic and anabolic to begin with because it is in a period of exponential growth. Kent et al. examined the effects of AA in lapine cartilage and found a positive effect, although previous and subsequent research failed to confirm this. [Kent, L. et al., "Differential Response of Articular Chondrocyte Populations to Thromboxane B2 and Analogs of Prostaglandin Cyclic Endoperoxidases," *Prostaglandins,* 19:391–406 (1980)]. Kirkpatrick and Gardner found that AA and various metabolites of AA had insignificant or inhibitory effects on biosynthesis. [Kirkpatrick C. J. and Gardner, D. L., "Influence of PGA1 on Cartilage Growth," *Experientia,* 33(4):504 (1976)]. Lippiello, et al. found, however, that AA and other omega-6 fatty acids had beneficial effects on chondrocyte metabolism in cell culture. [Lippiello, L., Ward, M., "Modification of articular cartilage chondrocyte metabolism by in vitro enrichment with fatty acids (abstract)," *Trans. Orthop. Res. Soc.* 13:162 (1988); Lippiello, L., "Prostaglandins and articular cartilage; does Prostaglandin perturbation perpetuate cartilage destruction?" *Semin Arthritis Rheum* 11:87 (1981).] These variable results are not unexpected, since the balance between anabolic and catabolic processes in the body is delicate and easily perturbed. Phan et al., suggest that products of AA via the cyclooxygenase pathway are anti-fibrogenic while AA products via the lipoxygenase pathway are pro-fibrogenic. This phenomenon demonstrates the complexity of the eicosanoids' interactions.

Catabolic events are typically mediated in the body by enzymes that break apart body constituents. Catabolism is essential for health and deficiency of necessary enzymes results in disease, such as the so-called storage diseases like mucopolysaccharhidosis. Excessive catabolism may also result in the breakdown of tissues and lead to disease, as in degenerative diseases like osteoarthritis or autoimmune diseases like multiple sclerosis. Various anti-catabolic substances in the body help contain and balance catabolism. For example, chondroitin sulfate counteracts metalloproteinases that catabolize collagen and proteoglycans in the cartilage matrix. Similarly, alpha-one anti-trypsin inhibits the effects of elastase, which contributes to alveolar breakdown in emphysema.

Oxidative damage also has an impact on the balance of anabolism and catabolism in the body. This damage is the result of the effects of free radicals, substances that have an unpaired electron. Free radicals form constantly in the body as the result of normal reactions like the production of ATP. They also form during the inflammatory process. Free radicals cause cellular damage because they are highly chemically reactive. Because they have only a single electron, (a condition that nature abhors as it does a vacuum), these substances "steal" electrons from molecules in their vicinity. The molecules making up cell structures, such as the cell membrane or DNA are thereby rendered electron-deficient. The deficiency of electrons in turn makes the cell structure unstable and cell dysfunction occurs, including manufacture of abnormal proteins, cell rupture, and cell death. Oxidative damage is implicated in many catabolic events in the body, including the aging process. Anti-oxidants, such as vitamin C, vitamin E, superoxide dismutase (SOD), selenium, and glutathione are substances that scavenge free radicals before oxidative damage occurs. In the sense that they prevent cell damage, anti-oxidants are a specific type of anti-catabolic agent.

The body also contains anabolic compounds that stimulate tissue growth. Glucosamine is an amino sugar naturally formed in the body from glucose. When supplied exogenously, glucosamine stimulates connective tissue cell synthesis, and thereby increases the amounts of normal extracellular matrix. Glucosamine is also the building block for glycosaminoglycans in cartilage and other connective tissues. Supplying additional glucosamine thus supplies the body with extra raw materials for matrix synthesis in connective tissues. Other examples of anabolic compounds in the body include somatotropin, which stimulates protein synthesis, and the somatomedins or insulin-like growth factors, which stimulate the proliferation of chondrocytes and fibroblasts and enhance matrix synthesis.

The actions and interactions of these compounds are complex. A given compound may have different effects in different tissues. For example, somatotropin increases protein synthesis (anabolism), but also speeds fat breakdown (catabolism). The effects that a particular compound or combination of compounds will have depend on many factors, including route of administration, dosage, and duration of therapy.

Previous researchers have investigated the use of individual compounds for their anabolic, anti-oxidant or anti-catabolic effects. Glucosamine has been found in cell culture to stimulate connective tissue cells to produce the components of the matrix: collagen and glycosaminoglycans (GAGs). [Jimenez, S., "The Effects of Glucosamine sulfate on Chondrocyte Gene Expression," *Eular Symposium,* Madrid October 1996 Proceedings, page 8–10]. S-adenosylmethionine is known to participate in several synthesis reactions, including the sulfation of GAGs. [Champe, P. *Biochemistry,* $2^{nd}$ edition, J. B. Lippincott Co, Philadelphia, 1994, pp. 248, 250, 265]. Arachadonic acid has been found to stimulate corneal healing. [Nakamura, M., "Arachidonic Acid Stimulates Corneal Epithelial Migration", *J. Ocul. Pharmacol., Summer:*10(2): 453–9 (1994)]. These compounds therefore have anabolic effects.

Chondroitin sulfate has been shown to inhibit degradative enzymes, including the metalloproteinases that destroy cartilage matrix. [Bartolucci, C., "Chondroprotective action of chondroitin sulfate," *Int. J. Tiss. Reac.*, XIII (6):311–317 (1991)]. Studies with pentosan sulfate have shown that it prevents complement-mediated damage in a rabbit myocardial cells. [Kilgore, K., "The Semisynthetic Polysaccharide Pentosan Polysulfate Prevents Complement-Mediated Myocardial Injury in the Rabbit Perfused Heart," *J. Pharmocol. Exp. Ther.,* 285(3):987–94 (1998)]. Oral administration of collagen type II has been shown to decrease the deleterious immune response that destroys joint tissue in rheumatoid arthritis. Tetracycline analogues are potent inhibitors of matrix metalloproteinases. [Ryan, M., "Potential of Tetracyclines to Modify Cartilage Breakdown in Osteoarthritis." [*Curr. Opin. Rheumatol.,* 8(3): 238–47 (1996)]. Diacerein modifies the inflammatory process by inhibiting interleukin-1 activity, and also by direct effects on lymphocytes and neutrophils. [Beccerica, E., "Diacetylrhein and rhein: in vivo and in vitro effect on lymphocyte membrane fluidity," *Pharmocol. Res.*, 22(3):277–85 (1990); Mian, M., "Experimental Studies on Diacerhein: Effects on the Phagocytosis of Neutrophil Cells from Subcutaneous Carregeenan-Induced Exudate," *Drugs Exp. Clin. Res.*, 13(11):695–8 (1987); Spencer, C., "Diacerein", *Drugs*, 53(1):98–106 (1997)]. These compounds can be classed as anti-catabolic agents.

L-ergothionine scavenges hydroxyl radicals and may inhibit singlet oxygen formation, [Han J S. "Effects of Various Chemical Compounds on Spontaneous and Hydrogen Peroxide Induced Reversion in Strain TA104 of *Salmonella typhimurium*," *Mutant Res.*, 266(2):77–84 (1992)], while superoxide dismutase scavenges superoxide radicals [Mathews C., *Biochemistry* $2^{nd}$ ed., Benjamin/Cummings Pub. Co., Menlo Park Calif., 1996, page 551]. These compounds can be classified as anti-oxidants.

Although these compounds have been investigated individually, to our knowledge no one other than the present inventors has examined the effects of certain combinations of any or all of anabolic, anti-catabolic and anti-oxidant agents to maintain health and to promote healing. According to the present invention, combinations of these agents can be used to maximize appropriate anabolic effects (healing) and decrease undesirable catabolic effects (degradation) and oxidative damage, while at the same time, causing minimal or no adverse reactions. Therefore, it can be seen that there exists a need to provide compositions that will make use of the beneficial effects of combinations of anabolic agents, anti-catabolic agents, anti-oxidant and/or analgesic agents for the maintenance and repair of connective tissues in humans and animals.

SUMMARY OF THE INVENTION

The present invention provides novel compositions and methods of treating repairing, and preventing damage to connective tissues in humans and animals using such compositions. Therefore, it is an object of the invention to provide novel compositions of any or all of anabolic, anti-catabolic, anti-oxidant and/or analgesic agents for the protection, treatment and repair of connective tissues in humans and animals.

It is another object of the present invention to provide methods of treating and repairing connective tissue in humans and animals with compositions containing any or all of anabolic, anti-catabolic, anti-oxidant and/or analgesic agents.

It is still another object of the present invention to provide compositions any or all of anabolic, anti-catabolic, anti-oxidant and/or analgesic agents selected from the group consisting of aminosugar, S-adenosylmethionine (SAMe), arachadonic acid (AA), GAG, pentosan sulfate, collagen type II, tetracyclines, diacerin, super oxide dismutase (SOD), L-ergothionine, one or more avocado/soybean unsaponifiables (ASUs) and analgesics, such as acetaminophen.

It is a further object of the present invention to provide compositions to repair, treat, and prevent damage to connective tissue in humans and animals that contain one or more of the elements selected from the group consisting of aminosugar, SAMe, arachodonic acid, GAG, pentosan sulfate, collagen type II, tetracyclines, diacerin, SOD, L-ergothionine, one or more ASUs and analgesics, e.g, acetaminophen.

These and other objects of the present invention are apparent from the detailed description and claims below.

DETAILED DESCRIPTION OF THE INVENTION

The compositions of the present invention, used to treat, repair, and prevent damage to connective tissue, include combinations of anabolic, anti-catabolic, and/or anti-oxidant agents. Ingredients of preferred embodiments include compositions selected from the group consisting of aminosugars, SAMe, AA, GAGs, including pentosan, collagen type II, tetracyclines, diacerin, SOD, L-ergothionine, and one or more ASUs. Optionally, the combinations of the present invention also include one or more analgesics, such as acetaminophen. In addition, the present invention covers methods of administering these novel compositions to humans and animals in need thereof.

Glucosamine—an example of an aminosugar—is naturally formed in the body from glucose. When supplied exogenously, glucosamine stimulates connective tissue cell synthesis, increasing the amounts of normal extracellular matrix. Glucosamine is also the building block for glycosaminoglycans ("GAGs") in cartilage and other connective tissues, thus, supplying additional glucosamine supplies the body with extra raw materials for matrix synthesis in connective tissues. The aminosugar component of the compositions of the present invention may comprise natural, synthetic or semi-synthetic aminosugars including but not limited to salts of glucosamine including glucosamine hydrochloride and glucosamine sulfate, glucosamine phosphate, and N-acetylglucosamine and salts and/or mixtures thereof. In addition, the term aminosugar is also used herein to encompass aminosugars that may have been chemically modified yet retain their function. Such chemical modifications include but are not limited to esterification, sulfation, polysulfation, acetylation, and methylation. Moreover, it is contemplated that the term aminosugar can extend to any composition of matter that is insubstantially different from the aminosugar as above-described.

The GAG component of the compositions of the present invention may comprise natural, synthetic or semisynthetic GAGs, GAG-like compounds, or GAG precursors, including but not limited to chondroitin, hyaluronic acid, glucuronic acid, iduronic acid, keratan sulfate, heparan sulfate, dermatin sulfate, and fragments, salts, and mixtures thereof. In addition, the term GAG as used herein further encompasses GAGs that have been chemically altered yet retain their function. Such modifications include but are not limited to esterification, sulfation, polysulfation, and methylation. In fact, sulfated GAGs are a preferred component of the compositions of the present invention. Hence, monosulfated and polysulfated (or oversulfated) GAGs are preferred GAG components of the compositions of the present invention. The term GAGs also is intended to encompass alternative nomenclature for the same group of above-described compounds—e.g., mucopolysaccharides, proteoglycans, and heparanoids. In addition, the GAG or GAG-like component of the compositions of the present invention may be derived from plant or animal sources, including but not limited to beechwood tree, to forms of animal cartilage including shark cartilage, bovine trachea, whale septum, and porcine nostrils, and to invertebrates such as *Perna canaliculus* and sea cucumber.

Chondroitin sulfate is a preferred GAG. Chondroitin sulfate is the most abundant glycosaminoglycan in articular cartilage and is also present in many other connective tissues in the body. Additionally, chondroitin sulfate competitively inhibits degradative enzymes that degrade connective tissues under conditions of abnormal, excessive inflammation. Chondroitin sulfate is a polymer composed of repeating units of glucuronic acid and sulfated galactosamine. [Lester M. Morrison, M. D. and O. Arne Schjeide, Ph.D., *Coronary Heart Disease and the Mucopolysaccharides (Glycosaminoglycans)* 12 (1974); Philip C. Champe and Richard A. Harvey, *Lippincott's Illustrated Reviews: Biochemistry*, 148–50 ($2^{nd}$ ed. 1994)]. One of ordinary skill in the art understands that chondroitin sulfate must have at least two, and potentially many, of these repeating units of glucuronic acid and sulfated galactosamine.

Figure 1:
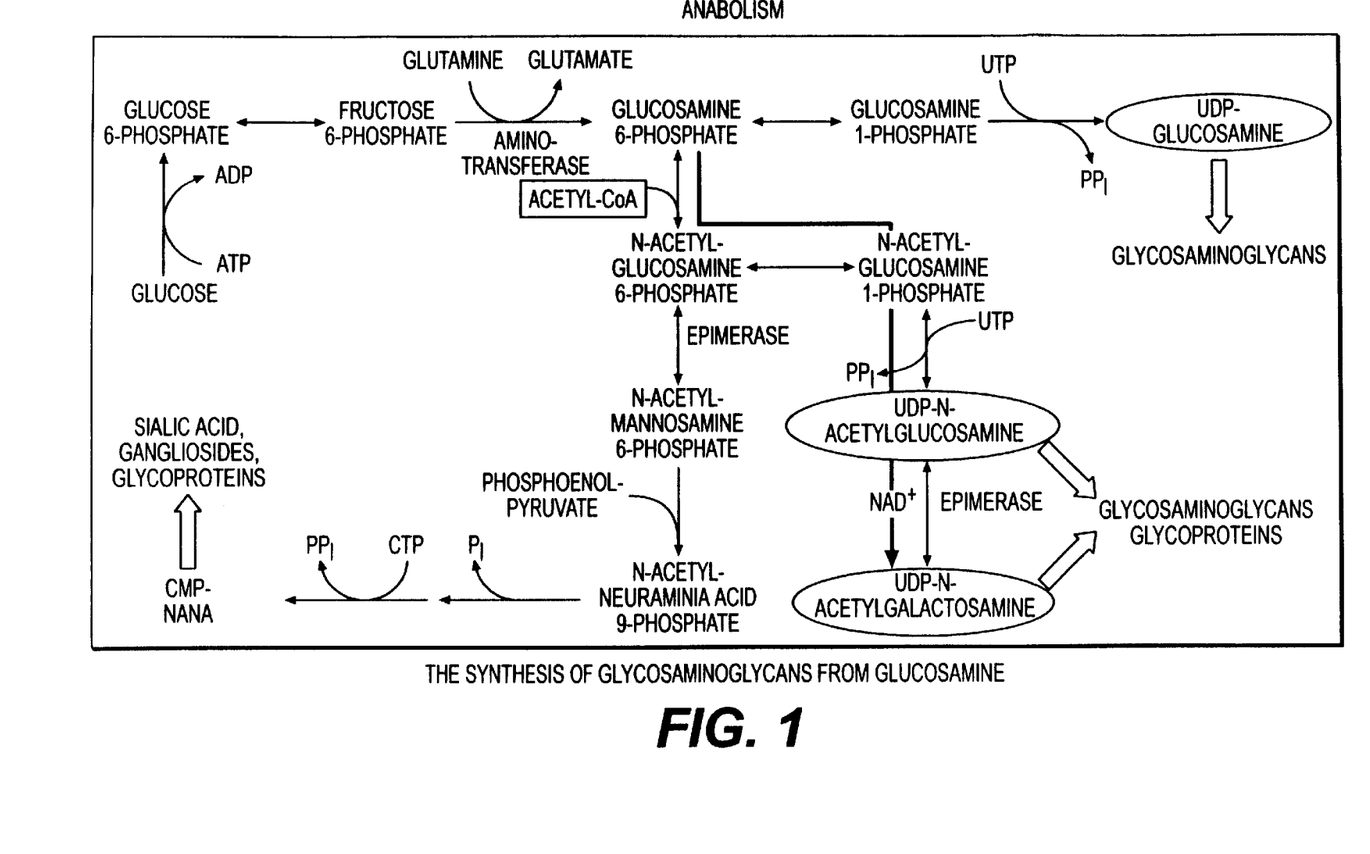
FIG. 1 provides a detailed description of the biosynthetic pathway for the creation of GAGs such as chondroitin sulfate.

FIG. 1 provides a detailed description of the biosynthetic pathway for the creation of GAGs, such as chondroitin sulfate. In addition, the present invention may include fragments of GAGs, such as fragments of chondroitin sulfate. One of ordinary skill in the art at the time the invention understands that "fragments of glycosaminoglycans" are groups of saccharides that constitute less than two repeating units of the glycosaminoglycan. Hence, it is understood that fragments of these substances would be composed of groups of saccharides that constitute fewer than two of the repeating units of the respective polymer.

For example, one of ordinary skill in the art understands that fragments of chondroitin sulfate are molecules composed of the saccharides that comprise the repeating units of chondroitin sulfate, but that are present in groups of less than the two repeating units described above. Thus, a molecule composed of a glucuronic acid and sulfated galactosamine would constitute a fragment of chondroitin sulfate. Indeed, there are eight different disaccharide structures that may constitute fragments of chondroitin sulfate. [Timothy E. Hardingham and Amanda J. Fosang, *Proteoglycans: Many Forms and Many Functions, FASEB J.*, 6:861–862 (1992)].

Other naturally occurring glycosaminoglycans may be used in this invention, for example, hyaluronic acid. Also, fragments of the glycosaminoglycans may also be utilized. A person of ordinary skill in the art understands the terms "fragments of chondroitin," "fragments of chondroitin sulfate," "fragments of chondroitin salts," "fragments of glycosaminoglycan" and "chondroitin sulfate fragments," and further understands them to mean groups of saccharides (or salts thereof) that constitute less than two repeating units of the glycosaminoglycan.

One of skill would expect that fragments of chondroitin sulfate, for example, would have the same utility as chondroitin sulfate itself. Chondroitin sulfate is broken down into smaller units within the body, and that it is reformulated in the production of cartilage and other connective tissue. Therefore, it is understood that the body utilizes fragments of chondroitin sulfate in the same manner as it utilizes chondroitin sulfate itself. The same is true with respect to "fragments of chondroitin," "fragments of chondroitin salts," and "fragments of glycosaminoglycan." Each of chondroitin, chondroitin salts and other glycosaminoglycans, if ingested, is broken down by the body and reformulated in the production of cartilage and other connective tissue. Therefore, the body utilizes fragments of chondroitin in the same manner as it utilizes chondroitin itself, utilizes fragments of chondroitin salts in the same manner as it utilizes chondroitin salts, and utilizes fragments of glycosaminoglycans in the same manner as it utilizes glycosaminoglycans.

Moreover, it is intended that the term GAG can extend to any composition of matter that is insubstantially different from the GAGs as above-described. An example of such a GAG-like compound that is within the scope of the present invention is pentosan polysulfate (PPS) as well as salts thereof such as calcium-derived PPS and sodium PPS. Accordingly, a preferred GAG-like compound that may be used in the compositions of the present invention is PPS.

PPS is a semi-synthetic polysulfated xylan that is a sulfated form of a compound extracted from beechwood hemicellulose consisting of repeating units of (1–4) linked β-D-xylano-pyranoses. More specifically, PPS is produced by extracting these hemicellulose compounds via a series of chemical reactions from the wood, and then adding numerous sulfate groups to the purified polysaccharide chains. This process results in low molecular weight linear polysaccharide chains that carry numerous negatively charged sulfate groups. PPS is a semi-synthetic heparinoid that is considered an oversulfated form of a GAG.

There are several forms of PPS that display the above-described activities. Sodium PPS and a calcium-derived PPS (called CAPPS) may both be used to accomplish the functions of PPS. Each of these forms of PPS exhibit GAG-like activity, and will hereinafter be referred to as GAG-like compounds.

Pentosan's mechanism of action can be summarized as follows:
1. Anti-inflammatory activities through stabilization and improvement of micro-circulation in the inflamed tissues and through anti-Complement effects (decreases the release of the humoral mediators of inflammation called the Complement cascade).
2. Inhibition of chemotaxis of granulocytes, which are white blood cells that contribute to inflammation.
3. Stimulatory effect on proteoglycan synthesis.
4. Stimulatory effects on hyaluronic acid synthesis by synovial fibroblasts.
5. Potent inhibition of catabolic enzymes including, human granulocyte elastase (noncompetitive inhibition), hyaluronidase (competitive inhibition), chondroitin-4-sulfatase and N-acetyl-glucosaminidase at concentrations much more lower than that of NSAIDs.

Other synthetic or semi-synthetic glycosaminoglycans or glycosaminoglycan-like compounds, such as polysulfated glycosaminoglycans, may be used in this invention.

Diacerein, a recently recognized organic compound found in plants of the genus Cassia has anti-inflammatory effects through inhibition of interleukin-1B consequently collagenase production in articular cartilage is reduced. It reduces the fibrinolytic activity of synovial fibroblasts as well. It also dose-dependently inhibits chemotaxis (attraction of white blood cells) and superoxide anion production (this is one of the "toxic oxygen species" or "free radicals"). These harmful compounds occur spontaneously in the body, especially during destructive inflammation. Diacerein has analgesic and antipyretic activities. It reduces the breakdown of chondroitin-4-sulfate resulting in an increase in the ratio of chondroitin-4-sulfate to chondroitin-6-sulfate. (This ratio is pathologically decreased in degenerating cartilage.) It mildly increases prostaglandin synthesis, which allows it to have protective effects on the gastric mucosa.

S-adenosylmethionine (SAMe) is an important endogenous compound, present throughout the body, and taking part in a great number of biologic reactions such as transsulfation reactions. In this role it is an important reactant in the synthesis of many structural components of connective tissues, including proteins and proteoglycans. Thus, SAMe has significant anabolic effects which would enhance the actions of other anabolic agents. SAMe also has anti-inflammatory effects by virtue of its antioxidant action.

Figure 2:
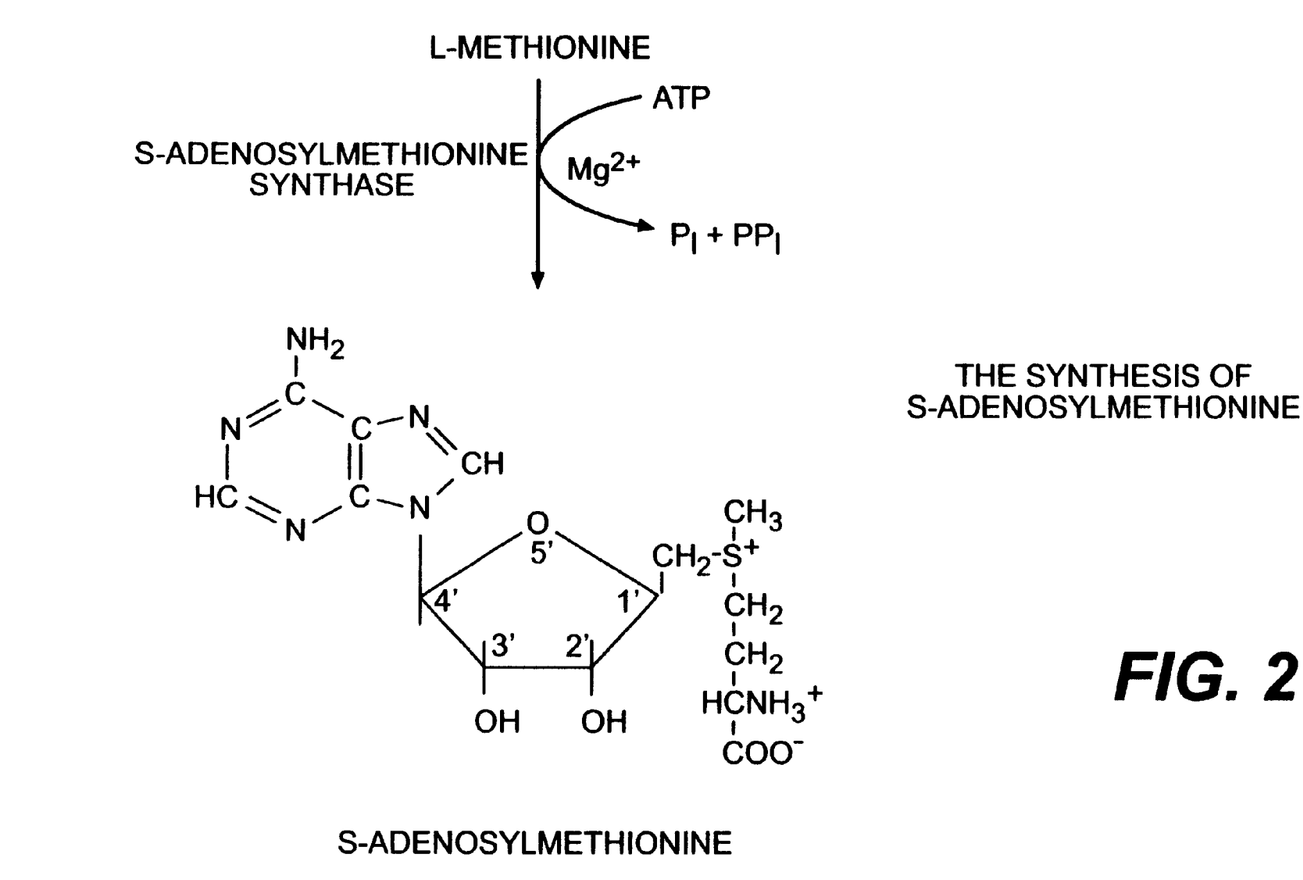
FIG. 2 is the molecular structure of SAMe and its immediate precursor.

SAMe is compound synthesized in the body from adenosine triphosphate ("ATP") and methionine (FIG. 2). It is present in many tissues, including the central nervous system. The primary CNS function of SAMe is to donate methyl groups in the reactions synthesizing various crucial compounds, including neurotransmitters and phospholipids. For example, SAMe facilitates the conversion of phosphatidylethanolamine to phosphatidylcholine, which forms part of the inner, lipid layer of the plasma membrane. In so doing, SAMe increases membrane fluidity and enhances effectiveness of receptor/ligand binding. [Champe and Harvey, Biochemistry, 1994; Stramentinoli, G., "Pharmacologic Aspects of S-Adenosylmethionine," *American J. Med.,* 83(5A):35 (1987); Baldessarini, F., "Neuropharmacology of S-Adenosyl Methionine," *American J. Med.,* 83(5A):95 (1987); Carney, M., "Neuropharmacology of S-Adenosyl Methionine," *Clin. Neuropharmacol.,* 9(3):235 (1986); Janicak, P., "S-Adenosylmethionine in Depression," *Alabama J. Med. Sci.* 25(3):306 (1988)]. These functions may also pertain to other methyl donors such as betaine (trimethylglycine), 5-methyltetrahydrofolate, folic acid, and dimethylglycine. [Champe and Harvey, *Biochemistry,* 1994].

Figure 3:
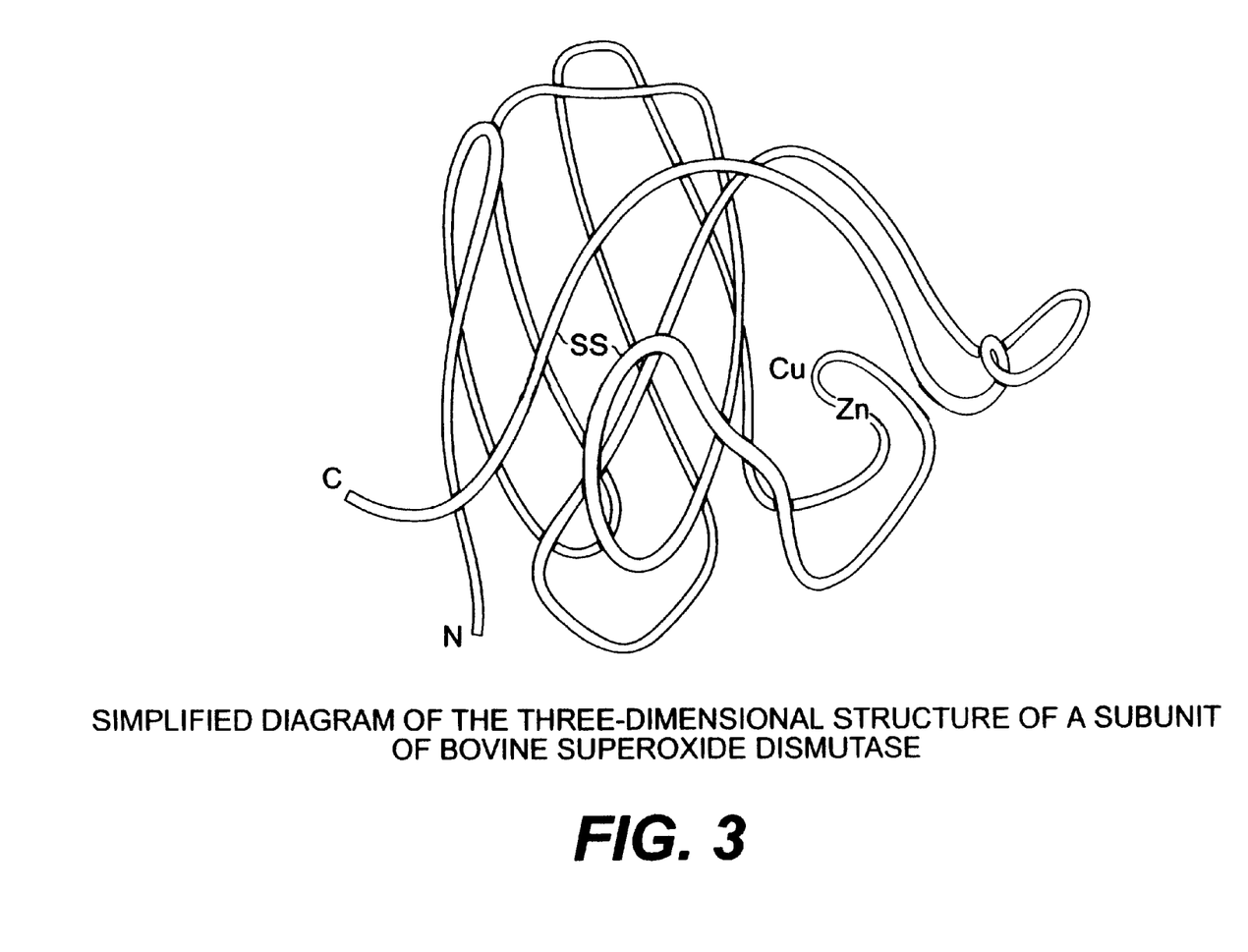
FIG. 3 provides a simplified diagram of the function of SOD.
Figure 4:
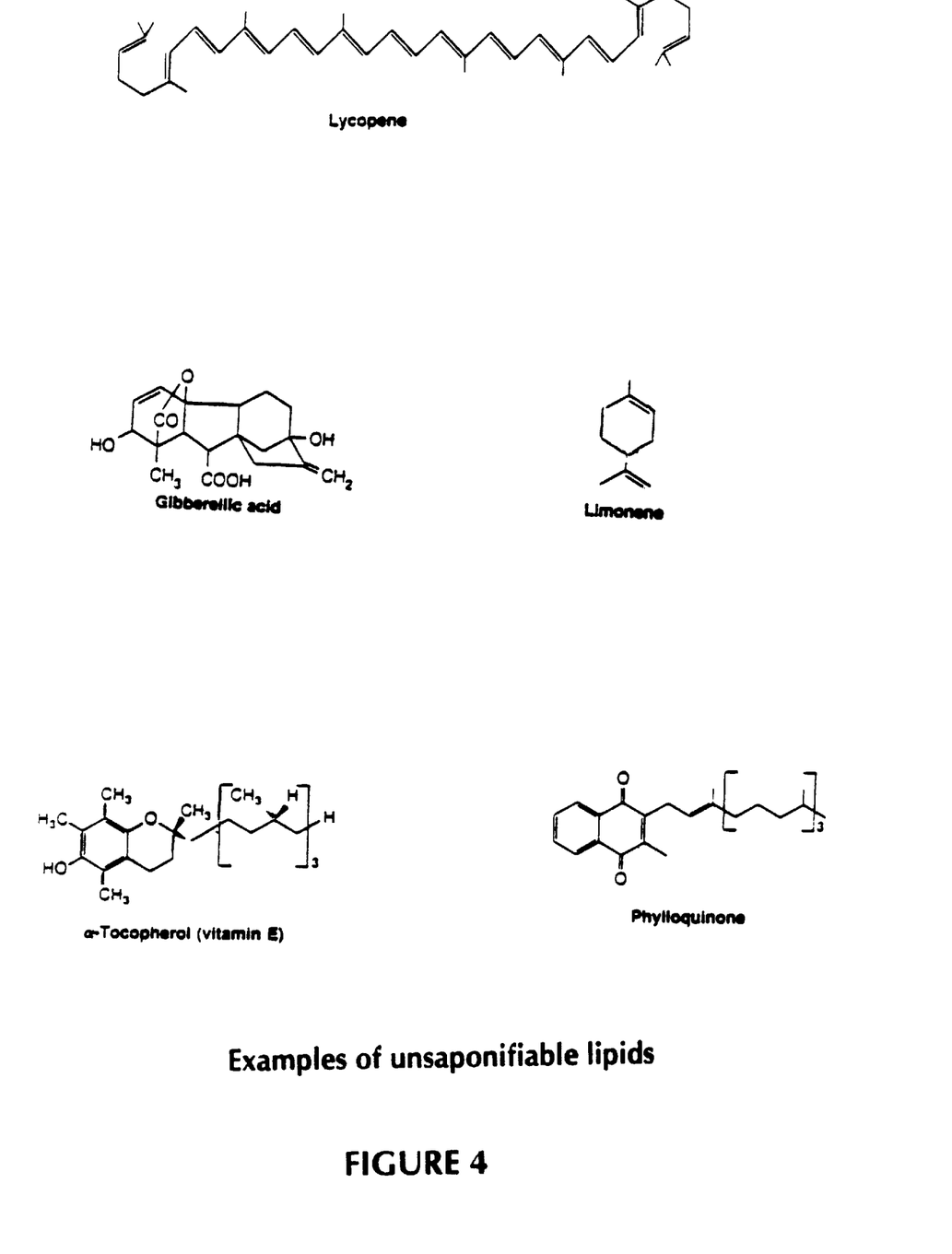
FIG. 4 provides some examples of unsaponifiable lipids.
Figure 5:
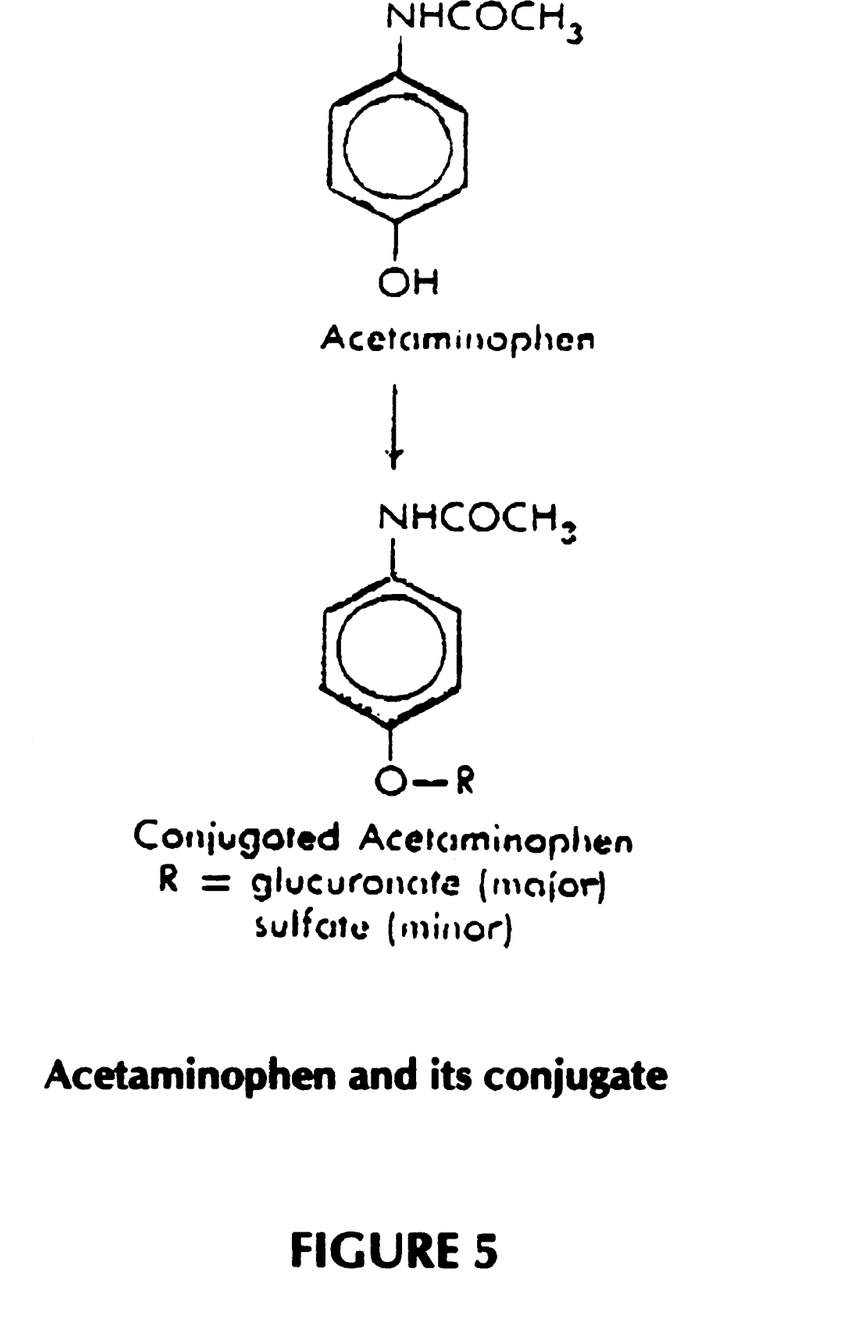
FIG. 5 is the molecular structure of acetaminophen.

Superoxide dismutase is an enzyme present naturally in the tissues of animals and plants, which has recently been investigated as an agent in the management of inflammation. It acts by intercepting toxic oxygen radicals in the intracellular space during destructive inflammatory processes. It does not inhibit prostaglandin biosynthesis, but stops the overproduction of prostaglandins resulting from destructive inflammation. Some of its effects include inhibition of edema formation and inhibition of acute signs of inflammation and the secondary articular changes (stiffness and calcification) in adjuvant-induced arthritis. Having no analgesic effects, it does not contribute to the overuse of the affected joints that eventually leads to more damage of the articular cartilage, as NSAIDs can. Also, it has no adverse effects on the cardiovascular, central nervous or endocrine systems. FIG. 3 provides a simplified diagram of the function of SOD.

L-ergothionine is an intracellular antioxidant naturally occurring in plants and animals, but not synthesized in human bodies: it comes only from dietary sources. The antioxidant properties of L-ergothionein appear to be related to its ability to scavenge reactive oxygen species (free radicals), chelate various metallic cations, activate antioxidant enzymes such as glutathione peroxidase (SeGPx) and manganese superoxide dismutase (Mn SOD) and to inhibit superoxide-generating enzymes such as NADPH-Cytochrome C reductase, and to affect the oxidation of various hemoproteins such as hemoglobin and myoglobin. Because all body tissues depend on these two oxygen carrier molecules, this characteristic is extremely beneficial. [Brummel, M. C., "In Search of a Physiological Function for L-ergothioneine," *Med. Hypotheses,* 18(4):351–70 (December 1985); Brummel, M. C., "In Search of a Physiological Function for L-ergothioneine,—II," *Med. Hypotheses,* 30(1):39–48 (September 1989); Han, J. S., "Effects of Various Chemical Compounds on Spontaneous and Hydrogen Peroxide-Induced Reversion in Strain TA104 of *Salmonella typhimurium,*" *Mutat. Res.,* 266(2):77–84 (April 1992); Arduini, A., "Possible Mechanism of Inhibition of Nitrite-Induced Oxidation of Oxyhemoglobin by Ergothioneine and Uric Acid," *Arch. Biochem. Biophys.,* 294(2):398–402 (May 1992)].

Collagen Type II also has beneficial effects that help maintain the normal balance between anabolism and catabolism. Specifically, connective tissue diseases may result from autoimmune processes, in which the immune system attacks and catabolizes the individual's own connective tissues as if it were a "foreign invader." Oral administration of collagen Type II can desensitize the immune system, preventing further attack and normalizing immune responses in these individuals. This decreases catabolic processes in the connective tissues and maximize anabolism. Ingestion of collagen type II presents this molecule to the immune cells in the gut-associated lymphoid tissues (GALT, a.k.a., Peyer's patches). Interactions between the collagen molecule and specific cells within the GALT activates mobile immune cells called T suppressor cells. These cells, in turn, moderate the destructive immune reaction against the individual's own collagen type II (in connective tissues).

Compounds in the tetracycline family include tetracycline, doxycycline, tetracycline analogs, and "tetracycline-like" compounds, and have been used therapeutically for their anti-microbial effects. Current research has focused on "tetracycline-like" compounds which possess insignificant antimicrobial effects, but with anti-catabolic effects. Specifically, "tetracycline-like" compounds are polycyclic compounds that inhibit tissue metalloproteinases which degrade extracellular matrix components including collagen and proteoglycans yet have insubstantial anti-microbial effects. This function of these compounds, as well as other compounds in the tetracycline family, may be related to the ability of these compounds to chelate calcium and zinc ions. For example, doxycycline has been shown to inhibit collagenase activity in articular cartilage.

Certain lipid extracts, termed nonsaponifiable, of avocado (genus Persea, especially *P. americana*) and the soybean (*Glycine max*) have also been studied for their beneficial effects on connective tissues. These nonsaponifiable compounds are that part of the plant lipids that do not undergo saponification, i.e., they do not react with alkali to form a soap. There are many such compounds, and any particular avocado extract may contain any number. Examples include fat soluble vitamins (A, D, E, and K), steroids such as phytoestrogens, sterols (bioflavonoids) and volatile essentials oils (terpenes such as menthol, camphor, lycopene, gibberellic acid, limonene, cinnamaldehyde, carotenoids, and ubiquinone, also known as coenzyme Q.) [Mathews, C. K. & van Holde, K. E. *Biochemistry,* $2^{nd}$ ed., The Benjamin/Cummings Pub. Co., Inc., 1996, p. 691.]

The avocado/soybean unsaponifiables (ASU) have been used in Europe under the trade name Piascledine and have been used to treat osteoarthritis and other forms of arthritis [Thiers, M. H., "Unsaponifiable constituents of avocado and soya oils. Treatment of certain forms of arthralgia," *J. Med. Lyon* 53(222):195–8 (February 1972) (article in French)], as well as soft-tissue inflammatory conditions [Trevoux, R., "Unsaponifiable fractions of the avocado and soybean in gynecology," *J. Bynecol. Obstet. Biol. Reprod.* 6(1):99–105 (January 1977) (article in French); Lamaud, M. E., et al., "Biochemical modifications of connective tissue induced by the non-saponifiables of avocado and soy-bean oils administered percutaneously in the 'hairless' rat," *Pathol. Biol.* 26(5):269–74 (May–June 1978) (article in French)]. The mechanism of action of this compound is to stimulate chondrocyte expression of TGF (transforming growth factor) beta 1, TGF beta 2 and plasminogen activator inhibitor 1 ("PAI-1"). By increasing PAI-1, ASU blocks the cascade that leads to metalloprotease activation [Boumediene K., et al., "Avocado/soya unsaponifiables enhance the expression of transforming growth factor beta 1 and beta 2 in cultured articular chondrocytes," *Arthritis Rheum.* 42(1): 148–56 (January 1999)]. ASU mixtures also reduce the spontaneous production of stromelysins, IL-6, IL-8 and prostaglandin E2 by chondrocytes. Additionally, ASUs decrease the effects of IL-1, and thereby reduce chondrocyte and synoviocyte production of collagenase. [Henrotin, Y. E., et al., "Effects of three avocado/soybean unsaponifiable mixtures on metalloproteinases, cytokines and prostaglandin E2 production by human articular chondrocytes," *Clin. Rheumatol.* 17(1): 31–9 (1998).]

TGF beta 1 and 2 are members of a family of homologous polypeptidecytokines. These locally-acting hormones can have paracrine or autocrine effects and are made by a variety of cell types, including lymphocytes, endothelial cells and macrophages. TGF beta has varied effects in different tissues; it generally inhibits epithelial cell metabolism. In connective tissues, however, it has been shown to be an indirect mitogen for fibroblasts and other cells of mesenchymal origin. It also can stimulate cellular production of fibronectin and collagen, and decrease protease activity, resulting in a net increase in matrix production. [Cotran, R. F., Kumar, V. and Robbins, S. L., Eds., *Pathologic Basis of Disease*, 5$^{th}$ ed., Saunders, 1994, pp. 40–42.]

Stromelysins are a subtype of proteinases that act on a variety of extracellular matrix components, including proteoglycans, laminin, fibronectin, and collagen. Stromelysins are produced by fibroblasts, synoviocytes, and macrophages, among other cell types, under the influence of cytokines such interleukin-1 and tumor necrosis factor alpha. Interleukins and prostaglandins are among the many mediators of inflammation. Reductions in levels of all of these compounds result in a decrease in pain and swelling, which are hallmarks of inflammation.

The fat-soluble vitamins present in ASU mixtures are necessary for growth, and augment the anabolic effects of TGF-beta. Because they stimulate TGF beta and also decrease degradative enzymes, as explained above, ASU mixtures can be said to have both anabolic and anti-catabolic effects. Although some of the effects of ASUs overlap the effects of other compounds in the present invention, ASUs contribute unique properties to the group of compounds and provide very beneficial effects when used in combination with those other compounds. For example, while glucosamine and ASUs both stimulate anabolic processes in connective tissue cells, these compounds have different cellular mechanisms of action. Glucosamine acts in part through protein kinase C, while the effect of ASUs, as stated above, is through transforming growth factor. Similarly, chondroitin and ASUs have inhibitory effects of IL-1. ASUs, however, inhibit the plasmin cascade, while chondroitin decreases activation of the complement cascade. Osteoarthritis is a complex disease involving interplay of many cytokines at the cellular level. Because the different compounds of the present invention act on different cytokines, they will have synergistic effects when used in appropriate combinations.

In placebo controlled, double blind trials, ASUs have been shown effective in reducing symptoms of osteoarthritis [Maheu, E., et al., "Symptomatic efficacy of avocado/ soybean unsaponifiables in the treatment of osteoarthritis," *Arthritis Rheum.* 41(1): 81–91 (January 1998); Blotman, F., et al., "Efficacy and safety of avocado/soybean unsaponifiables in the treatment of symptomatic osteoarthritis," *Rev. Rheum. Engl. Ed.* 64(12): 825–34 (December 1997)]. In these studies, side effects in the intervention groups were similar to those seen in the placebo groups, indicating that ASUs are safe and well tolerated substances. ASUs as used in this invention can include any or all unsaponifiable lipids and/or combinations thereof. Examples of components of ASUs include but are not limited to: limonene, beta carotene, phyloquinone, and giberellic acid. As explained above, ASUs can include any of a number of classes of compounds including but not limited to fat soluble vitamins, steroids, sterols and volatile essentials oils, or any combinations thereof. The invention includes, moreover, compositions which contain one avocado/soybean extract (ASU) or mixtures or combinations of such extracts (more than one ASU). There are many such combinations and all are intended to be included within the present invention.

The compounds of the present invention have several advantages over existing therapies for connective tissue disorders, such as excellent safety profiles. This is in part related to the fact that these compounds occur normally in the body and in various foods. Another characteristic shared by the compounds is tendency for a slow onset of action. Pharmaceuticals, such as NSAIDs, tend to cause sudden changes in the symptoms of disease. The endogenous compounds in the present invention work more slowly, by normalizing structures and functions within the body. While this action is beneficial, it does mean that symptoms will typically not be relieved immediately. For this reason, an analgesic is included as an optional component of the compositions of the present invention. The analgesic is to be chosen from the group of analgesic compounds that have been shown to have minimal side effects at therapeutic doses, and also to have minimal negative effects on connective tissue synthesis, as corticosteroid drugs and many NSAIDs have been shown to have. The analgesic that may be included in the composition of the present invention therefore is a nonsteroidal analgesic that does not have anti-inflammatory effects. In other words, the analgesic is a nonsteroidal drug that is not an NSAID. Examples of the analgesics of the present invention include acetaminophen and tramadol. Except as discussed below, the preferred analgesic of the present invention is acetaminophen.

Acetaminophen is an analine derivative analgesic and antipyretic compound working centrally through reversible inhibition of the enzyme cyclo-oxygenase in the central nervous system. Acetaminophen also blocks the peripheral pain impulse generation in nerve endings throughout the body. It has been used extensively for symptomatic pain relief. The relief of pain is beneficial for more than the obvious humane reasons. Since there are also important links between the emotional centers of the brain and the immune system, the relief of pain, and the resulting elevation in mood, has beneficial effects on inflammation and the many other processes that are modulated by the immune system. Although it blocks cyclooxygenase activity, acetaminophen has very little anti-inflammatory activity. Therefore, acetaminophen does not inhibit connective tissue anabolism, as NSAIDs and corticosteroids do, and because it has minimal side effects at therapeutic doses, it is an ideal analgesic agent in the present invention. Another advantage to including a safe analgesic in the present invention is that it will increase the likelihood that patient compliance would be high, i.e., that patients would continue taking the preparations long enough for disease-modifying effects to occur. Studies of isolated chondroprotective agents often have a high rate of drop-out in the early weeks of therapy due to patient perception that the agent is not working. With the addition of an analgesic, patients would be more inclined to continue therapy.

Cats are sensitive to acetaminophen because they do not metabolize it effectively (poor hepatic conjugation with glucuronic acid and subsequent depletion of glutathione occurs) [Goodman, A. and Goodman, L., *The Pharmacological Basis of Therapeutics*, 7$^{th}$ ed., MacMillan Publishing Co., 1985, pp. 692–95; Ahrens, F., *Pharmacology*, Williams & Wilkins, 1996, pp. 174–75]. Accordingly, acetaminophen is not recommended for use in cats.

The present invention comprises novel combinations of anabolic agents, anti-catabolic agents and antioxidant agents that maximize beneficial, anabolic effects (healing) and minimize any potential negative effects. In so doing, the present invention provides novel combinations of these agents and anti-oxidant agents, for the protection, treatment and repair of connective tissues in humans and animals.

These compounds have a variety of beneficial effects on animal and human connective tissues, and, because they function via a variety of mechanisms, work well in combination with each other. Although each compound has a number of functions, they can be roughly grouped as: (1) anabolic agents, including glucosamine, SAMe, AA, and ASUs, which promote growth processes in the body; (2) anti-catabolic agents, such as chondroitin sulfate, pentosan sulfate, collagen type II, tetracyclines, diacerin and ASUs, which inhibit destructive or catabolic processes; and (3) antioxidants, such as SOD, and L-ergothionine which prevent tissue damage by scavenging toxic oxygen species (free radicals). Naturally, some compounds, such as ASUs, could be placed in more than one group, by virtue of their overlapping functions. The present invention establishes that combinations of these compounds would work well. In addition, an analgesic could optionally be added to any of the individual compounds recited above or to a combination of them to provide relief from pain. Acetaminophen is the analgesic of choice because it does not have powerful anti-inflammatory effects and therefore does not interfere with healing of connective tissue. It also has minimal side effects at therapeutic doses, unlike NSAIDs which may cause gastrointestinal ulceration or poor renal perfusion even at therapeutic doses. Thus, the present invention consists of various combinations of two or more of the following agents: AA, glucosamine, chondroitin sulfate, pentosan, diacerin, S-adenosylmethionine, superoxide dismutase, L-ergothionein, collagen type II, tetracycline-like compounds, one or more ASUs and, optionally, one or more analgesics, e.g., acetaminophen. Examples include, but are not limited to such combinations as: two anabolic agents (e.g., AA and glucosamine); an anabolic agent and an anti-catabolic agent (e.g., AA and pentosan); an anti-catabolic and an antioxidant (e.g., tetracyclicline and superoxide dismutase); or combinations of more than two agents (e.g., glucosamine, SAMe and AA) or SAMe, ASUs, acetaminophen and diacerin. Examples of specific compounds that may be present in ASU extracts include but are not limited to: limonene, beta carotene, ubiquinone, and undecaprenol phosphate.

The following table shows possible combinations of pairs of the compounds discussed above. The letter "X" marks novel combinations of compounds that form the novel compositions of the present invention. The invention also includes combinations of three or more agents of the following compounds in the combinations shown on the table:

Glucosamine
Chondroitin
SAMe
Pentosan
Superoxide Dismutase (SOD)
L-Ergothionine
Collagen Type II
Diacerin
Arachadonic Acid
Tetracycline like compounds
One or more avocado/soybean unsaponifiables.
Analgesic, e.g., acetaminophen As explained above, examples of desired combinations are marked by X. For example, the first X in the first row means a combination of glucosamine and L-ergothionine or glucosamine and diacerin. The compositions of the present invention additionally comprise any aggregation or addition of the combinations marked by X in any given row or column. For example, the compositions disclosed in the first row include combinations of glucosamine plus L-ergothionine plus diacerin, or glucosamine plus diacerin plus tetracycline-like compounds or glucosamine plus L-ergothionine plus diacerin plus AA plus tetracycline-like compounds, and so on. Examples of compositions disclosed in the column designated "Collagen Type II" would include combinations of collagen Type II plus SAMe plus pentosan, or collagen Type II plus SAMe plus pentosan plus superoxide dismutase plus L-ergothionine, and so on. Examples of compositions disclosed in the column designated "ASU" would include combinations of one or more ASUs plus glucosamine, or one or more ASUs plus SAMe plus pentosan, or one or more ASUs plus collagen Type II plus SAMe plus pentosan plus superoxide dismutase plus L-ergothionine, and so on. Similarly, the table shows that an analgesic, e.g., acetaminophen, can be combined with any other compound listed in the table either singly or in any combination.

|  | Superoxide Dismutase (SOD) | L-Ergothionine | Collagen Type II | Diacerin | Arachadonic Acid | Tetracycline like compounds | ASU | Analgesic, e.g., Acetaminophen |
|---|---|---|---|---|---|---|---|---|
| Glucosamine |  | X |  | X | X | X | X | X |
| Chondroitin |  | X |  | X | X | X | X | X |
| SAMe | X | X | X | X | X | X | X | X |
| Pentosan | X | X | X | X | X | X | X | X |
| Superoxide Dismutase (SOD) |  | X | X | X | X | X | X | X |

-continued

| | Superoxide Dismutase (SOD) | L-Ergothionine | Collagen Type II | Diacerin | Arachadonic Acid | Tetracycline like compounds | ASU | Analgesic, e.g., Acetaminophen |
|---|---|---|---|---|---|---|---|---|
| L-Ergothionine | | | X | X | X | X | X | X |
| Collagen Type II | | | | X | X | X | X | X |
| Diacerin | | | | | X | X | X | X |
| Arachadonic Acid | | | | | | X | X | X |
| Tetracycline like compounds | | | | | | | X | X |
| ASU | | | | | | | | X |

The present inventors have investigated certain combinations of the above agents and have documented a novel response in several combinations. The effects of certain combinations of chondroitin sulfate, glucosamine, SAMe, arachidonic acid, collagen, pentosan, and superoxide dismutase were studied in cultures of adult bovine cartilage cells in different experiments (see example 2). Certain combinations had an inhibitory effect (hypometabolic) in this particular study. Both stimulatory and inhibitory novel interactions could be beneficial under various disease states. For example, a hypermetabolic state is part of the pathogenesis of some diseases. In such diseases, an inhibitory (hypometabolic) response would be beneficial to the individual. Future studies are planned to investigate the effects of a range of concentrations in the agents studied under various experimental models. Note that both increases and decreases in biosynthetic activity are novel interactions and could be beneficial to organisms under selected circumstances. For example, many researchers currently believe that osteoarthritis has a hypermetabolic component, especially in the early stages of pathogenesis. Researchers are divided as to whether treatment should focus on agents that stimulate cartilage matrix production, or agents that are inhibitory and therefore make the cartilage environment more hypometabolic, which in turn could have a stabilizing effect on the cartilage tissue.

The compositions of the present invention may be administered via any route, including but not limited to intramuscularly, intravenously, orally, subcutaneously, rectally, topically, transcutaneously, intranasally, and intra-articularly, sublingually, intraperitoneally. Also, any salt of any of the present compounds may be used to aid in absorption, e.g., glucosamine HCl, glucosamine sulfate, glucosamine phosphate, sodium chondroitin sulfate, calcium chondroitin sulfate, potassium chondroitin sulfate, etc. In addition, the composition can be given in all common dosage forms including extended release dosage forms, pills, tablets, capsules, creams, liquids, aerosols, extended release forms, injectables, etc.

The dosage ranges of the compositions of the present invention will vary depending upon the needs of the human or animal to which the compositions are administered. The dosage ranges for the various components of the presently claimed compositions are as follows:

| Compound | Daily Dose |
|---|---|
| Glucosamine | Total dose range: 25 mg to 12 g<br>Small animal: 25 mg–3 g. |
| Chondroitin sulfate | Human: 100 mg–4 g<br>large animal: 300 mg–12 g<br>Total dose range: 15 mg–12 g<br>Small animal: 15 mg–2 g |
| SAMe | Human: 75 mg–4 g<br>large animal: 300 mg–12 g<br>Total dose range: 10 mg–8 g<br>Small animal: 10 mg–1 g |
| Pentosan | Human: 75 mg–3 g<br>large animal: 400 mg–8 g<br>Total dose range: 3 mg to 3 g<br>Small animal: 3 mg–1 g |
| Superoxide dismutase | Human: 50 mg–2 g<br>large animal: 100 mg–3 g<br>Total dose range: 3 mg to 6 g<br>(each mg containing > 3000 McCord–Fridovich units)<br>Small animal 3 mg–2 g |
| L-ergothioneine | Human: 5 mg–3 g<br>large animal: 50 mg–6 g<br>Total dose range: 50 mg to 25 g<br>Small animal: 50 mg–10 g |
| Collagen Type II | Human: 50 mg–15 g<br>large animal: 100 mg–25 g<br>Total dose range: 0.1 mg to 10 g<br>Small animal: 0.1 mg–10 g |
| Diacerin | Human: 0.1 mg–7.5 g<br>large animal: 1.0 mg 10 g<br>Total dose range: 5 mg to 5 g<br>Small animal: 5 mg–1 g |
| Arachadonic acid | Human 20 mg–3 g<br>large animal: 50 mg–5 g<br>Total dose range: 10 mg to 12 g<br>Small animal: 10 mg–3 g |
| Tetracyclines | Human: 10 mg–5 g<br>large animal 50 mg–12 g<br>Total dose range: 1.0 mg to 2 g<br>Small animal: 1.0 mg–1 g |
| Avocado/soybean unsaponifiables | Human: 2 mg–1.5 g<br>large animal: 50 mg–2 g<br>Total dose range: 5 mg to 5 gram<br>Small animal: 5 mg to 1000 mg<br>Human: 50 mg to 1500 mg<br>Large animal: 100 mg to 5 grams<br>Or: 1 mg/kg to 25 mg/kg |
| Analgesic, e.g., acetaminophen | Total dose range: 4 mg to 10 grams<br>Small animal<br>(excluding cats): 4 mg to 1000 mg<br>Human: 100 mg to 4 gram<br>Large animal: 100 mg to 10 grams |

Doses are designed to cover the spectrum of body weights of small animals to large animals, with humans in the middle. The following examples are illustrative and do not in any way limit the present invention.

EXAMPLE 1

In our preliminary investigations, surgical instability was induced in the stifle joint of New Zealand white rabbits by modification of the Hulth technique. Post-operatively, animals were exercised for 1 hour daily. Experimental dietary formulas were evaluated for their cartilage stabilizing effect. The standard Harland (Teklad) rabbit diet (control); a standard diet also containing a 2% fungal oil containing 40% AA by weight (Arasco); and a standard diet containing also arachidonic acid and glucosamine/chondroitin were investigated. At 16 weeks, the medial femoral condyles of all rabbits were removed and cartilage degeneration quantitatively evaluated with a modified Mankin histological-histochemical grading system with safranin-O stained slides. Cartilage from all joints with surgical instability exhibited varying degrees of macroscopic degenerative lesions. Our preliminary results indicated that adding arachidonic acid to glucosamine/chondroitin sulfate has the potential to produce a novel interaction in cartilage. This novel interaction has the potential to have a cartilage modulating effect.

EXAMPLE 2

Procedure:

Articular cartilage was resected from human or animal joints aseptically and placed into a large petri dish in a small amount of DMEM/F-12 or F-12. The tissue was diced to 1–2 mm dimensions and transferred to a small culture flask containing 20 mL DMEM or F-12+400 u/mL collagenase. The flask was placed on the shaker and incubated overnight.

The cell digest was repeatedly aspirated to increase release of cells. The cell digest was then placed into a 50 mL sterile centrifuge tube and centrifuged in the Beckman at 1000 RPM for 10 minutes. The medium was discarded by pipette and fresh DMEM/F-12 containing 1% FCS added. Depending on the size of the pellet, about 20–40 mL medium was added. Cell counts were determined by haemocytometer and the digest made up to a concentration of 100,000 cells/0.2 mL.

GAG Synthesis:

To conduct GAG synthesis, 0.2 mL was aliquoted into each well of a 96 well plate using an 8 channel pipetter and the cells allowed to attach for 24 hours. The media was removed and 0.3 mL of fresh 1% FCS media added for 2–3 days. On the day of the experiment, the media was removed and the experimental solutions containing 35-sulfate isotope were added. The incubation was continued for 4 hours. Termination: at the end of the incubation period, the labeling media was removed, the cell layer was rinsed repeatedly with cold 0.3 mL DMEM or F-12 (about 5x), and the cell layer was frozen for counting.

Counting of 96 Well Plates:

The cell layer for both the synthesis experiments were heated at 50 degrees after adding 100 ul 1 N NaOH for a period of 2 hours. 200 ul scintillant was added and the plates were placed in the counter. The data was expressed as CPM/100,000 cells.

| Evaluation Agent | Indv. Agents: CPM/ 100,000 cells | Sum (CPM) | Agents Combined (CPM) | Difference (CPM) |
|---|---|---|---|---|
| ChSO4-L | 64 | | | |
| AA | 70 | 134 | 18 | −116 |
| ChSO4-H | 50 | | | |
| AA | 70 | 120 | 81 | −39 |
| Glu-H | 117 | | | |
| AA | 70 | 187 | 16 | −177 |
| 1% Sam | 123 | | | |
| 10Paleos | 86 | 209 | 62 | −147 |
| 1% Sam | 123 | | | |
| 1Paleos | 74 | 197 | 80 | −117 |
| 3% Sam | 42 | | | |
| 1Paleos | 74 | 116 | 100 | −16 |
| 3% Sam | 42 | | | |
| 10Paleos | 86 | 128 | 83 | −45 |
| 3% Sam | 42 | | | |
| Collagen | 118 | 160 | 90 | −70 |
| 3% Sam | 42 | | | |
| AA | 70 | 112 | 104 | −8 |
| AA | 70 | | | |
| 10Pentos | 76 | 146 | 106 | −40 |
| Collagen | 70 | | | |
| 10Paleos | 86 | 156 | 82 | −74 |
| Collagen | 118 | | | |
| 10Pentos | 76 | 194 | 65 | −129 |
| Collagen | 118 | | | |
| 10Paleos | 86 | 204 | 77 | −127 |

ChSO4 = Chondroitin
AA = Arachadonic Acid
SAMe = S-adenosylmethionine
Paleos = SOD
Collagen = Collagen
Pentos = Pentosan
H = High concentration
L = Low concentration In this model, at the concentrations studied, the representative combinations had an inhibitory (hypometabolic) effect in this particular study. This hypometabolic effect could be beneficial under various disease states, indeed both stimulatory and inhibitory novel interactions could be beneficial under various disease states. For example, a hypermetabolic state is part of the pathogenesis of some diseases. In such diseases, an inhibitory (hypometabolic) response would be beneficial to the individual. Future studies are planned to investigate the effects of a range of concentrations in the agents studied under various experimental models. Note that both increases and decreases in biosynthetic activity are novel interactions and could be beneficial to organisms under selected circumstances. For example, many researchers currently believe that osteoarthritis has a hypermetabolic component, especially in the early stages of pathogenesis. Researchers are divided as to whether treatment should focus on agents that stimulate cartilage matrix production, or agents that are inhibitory and therefore make the cartilage environment more hypometabolic, which in turn could have a stabilizing effect on the cartilage tissue.

EXAMPLE 3

A 4 year old child has juvenile rheumatoid arthritis in which the immune system inappropriately targets endogenous connective tissues with antibodies against native collagen type II. The resulting inflammation and degradation of cartilage causes pain and dysfunction in the synovial joints. Present treatments include corticosteroids which non-selectively suppress the immune system, thus leaving the body vulnerable to infectious disease, or methotrexate, which inhibits DNA synthesis, repair, and cellular replication, thus affecting not only the immune system but also intestinal mucosa, and the bone marrow. This child is given 2 mg of collagen type II daily, and SOD 10 mg daily. The collagen decreases the inappropriate immune attack, and the SOD inactivates destructive free radicals that damage cells. By preventing cellular damage, the SOD helps maximize the normal function of joint tissue cells. This combination has no harmful side effects at therapeutic doses and is a beneficial addition to existing therapies for rheumatoid arthritis.

EXAMPLE 4

A 6 year old thoroughbred race horse has neutrophilic inflammation of the carpus. In this condition, trauma to the tissues of the joint injures cells and therefore results in liberation of cytokines which attract large numbers of neutrophils into the synovial space. This response is beneficial in cases of sepsis, but in non-septic conditions the neutrophils provide no useful service to the animal. Indeed, because neutrophils produce various degradative compounds, including superoxide molecules, their presence in the joint contributes to a vicious cycle of inflammation, tissue damage, and increased inflammation. Currently this condition is treated with nonsteroidal antiinflammatory drugs, which suppress prostaglandin synthesis and therefore have many side effects. This horse is given a mixture of diacerin 100 mg, pentosan 200 mg and SAMe, 1000 mg The diacerin and pentosan both inhibit chemotaxis (the attraction of white blood cells into the affected area) and thus reduce the numbers of neutrophils in the joint. Additionally, pentosan stimulates the synthesis of synovial fluid and thus supports normal function of the joint. Diacerin inhibits superoxide production; since superoxide production is one of the mechanisms through which neutrophils have their harmful effects, this action of diacerin is obviously beneficial. SAMe supports the structure and function of cell membranes, and therefore helps repair injured joint tissue cells thus blocking the events that start the harmful inflammation. This combination has no harmful side effects at therapeutic doses and is a great improvement over existing therapies.

EXAMPLE 5

A 47 year-old woman has severe knee osteoarthritis. Currently she requires large doses of NSAIDs to control her symptoms. Although her orthopedic surgeon has recommended taking glucosamine/chondroitin sulfate, she has been reluctant to do so because these compounds are extracted from animal tissues and the patient is a strict vegetarian. Instead she takes diacerein 25 mg and ASU 250 mg, and 500 mg of acetaminophen daily. The diacerin inhibits chemotaxis and thereby reduces inflammation in the knee joint. The ASU increases TGF beta 1 and 2, stimulating repair of damaged joint tissues. The acetaminophen causes rapid analgesia, reducing the patient's symptoms without adversely affecting cartilage metabolism and without risk of gastrointestinal ulceration. As a result of the reduction in pain, the patient decides to add a 15 minute walk to her daily schedule. The controlled exercise further improves her physical and mental state.

EXAMPLE 6

A 5 year old Jersey dairy cow is diagnosed with severe osteoarthritis following an episode of fever and synovitis attributed to Lyme disease. This animal is the source of the owner's family milk supply and the owner wishes to treat the lameness with compounds that are "natural," i.e., compounds that normally occur in plants and animal bodies, rather than pursuing more traditional solutions such as 1) culling the animal 2) using non-steroidal anti-inflammatory drugs or 3) using steroids. The animal is treated with ASU 900 mg, SAMe 600 mg and glucosamine 500 mg daily. This approach is an improvement over existing options for several reasons. Because the compounds are natural components of plants and animal bodies with documented wide margins of safety, there is less concern over metabolites secreted in the milk. Because the compounds are available orally, and are active in small amounts, they are easy to administer to the animal in feed. The combined effect of the three compounds is to reduce inflammation and pain, to support normal function, and to stimulate healing of connective tissues.

Based on the teaching of the present invention, one of skill in the art would understand that combinations of the compounds taught by the present invention would act synergistically. For example, it is understood that glucosamine has stimulatory effects on chondrocyte metabolism which, by itself, aids in ameliorating diseases of cartilage degradation. However, an increase in cell metabolism can also produce an increase in free-radical production, as a natural by-product of oxidative phosphorylation. The increase in free radical production would dilute the beneficial effects of the glucosamine administration. By combining L-ergothioneine with glucosamine, one would expect an increase in metabolism and a reduction in free-radical damage, providing for a greater benefit than if compounds leading to one of these effects were provided. Therefore, one of skill in the art, based on the teaching of the present invention, would understand that combining glucosamine with L-ergothioneine would be more beneficial than providing either alone. The synergy that exists between certain compounds in the present invention also enables the use of lower doses of each compound. Although these compounds are quite safe, there may be a potential for side effects. For example, large doses of glucosamine sulfate or chondroitin sulfate can cause gastrointestinal disturbances in some individuals. In addition, these compounds are costly; for these reasons, the ability to minimize the dose and still achieve beneficial effects is desirable.

Many modifications may be made without departing from the basic spirit of the present invention. Accordingly, it will be appreciated by those skilled in the art that within the scope of the appended claims, the invention may be practiced other than has been specifically described herein. Hence, the attached claims are intended to cover the invention embodied in the claims and substantial equivalents thereto.

We claim:

1. A composition for the treatment, repair or prevention of damage to connective tissue comprising:

a synergistic combination of an aminosugar and avocado/soybean unsaponifiables.

2. The composition of claim 1, wherein the aminosugar is selected from the group consisting of glucosamine, glucosamine salts, and mixtures thereof.

3. The composition of claim 2, wherein the glucosamine salt is selected from the group consisting of glucosamine hydrochloride, glucosamine sulfate, N-acetylglucosamine and salts thereof.

4. The composition of claim 1, wherein the synergistic combination is administered orally, sublingually, nasally, gutturally, rectally, transdermally, or parenterally.

* * * * *